(12) United States Patent
Chen et al.

(10) Patent No.: US 8,709,495 B2
(45) Date of Patent: Apr. 29, 2014

(54) HIGHLY STABLE ELECTROLYTIC WATER WITH REDUCED NMR HALF LINE WIDTH

(75) Inventors: Yongge Chen, Guangdong (CN); Roberto De Noni, Fregona (IT)

(73) Assignee: APR Nanotechnologies S.A., Balerna (CH)

( * ) Notice: Subject to any disclaimer, the term of this patent is extended or adjusted under 35 U.S.C. 154(b) by 653 days.

(21) Appl. No.: 12/597,587

(22) PCT Filed: Apr. 25, 2008

(86) PCT No.: PCT/EP2008/003383
§ 371 (c)(1),
(2), (4) Date: Jan. 29, 2010

(87) PCT Pub. No.: WO2008/131936
PCT Pub. Date: Nov. 6, 2008

(65) Prior Publication Data
US 2010/0119616 A1    May 13, 2010

Related U.S. Application Data

(60) Provisional application No. 60/926,182, filed on Apr. 25, 2007.

(51) Int. Cl.
*A61K 33/00* (2006.01)
*C25B 1/04* (2006.01)
*C25B 9/08* (2006.01)
*A61P 17/00* (2006.01)
*A61P 17/02* (2006.01)

(52) U.S. Cl.
USPC .......................... 424/600; 205/464; 204/252

(58) Field of Classification Search
USPC .......................................................... 424/600
See application file for complete search history.

(56) References Cited

U.S. PATENT DOCUMENTS

| 5,234,563 A | 8/1993 | Arai et al. |
| 5,334,383 A | 8/1994 | Morrow |
| 5,445,722 A | 8/1995 | Yamaguti et al. |

(Continued)

FOREIGN PATENT DOCUMENTS

| EP | 0933332 | 8/1999 |
| EP | 1036861 A1 | 9/2000 |

(Continued)

OTHER PUBLICATIONS

Venkitanarayanan, K. S., et al. "Efficacy of Electrolyzed Oxidizing water for inactivating *E. coli* 0157:H7, *Salmonella enteritidis*, and *Listeria monocytogenes*." Applied and Environmental Microbiology, 1999, v. 65, iss. 9, 4276-4279.*

(Continued)

*Primary Examiner* — Mina Haghighatian
*Assistant Examiner* — Erin Hirt
(74) *Attorney, Agent, or Firm* — Clark G. Sullivan; Troutman Sanders LLP

(57) ABSTRACT

Electrolytic acid or alkaline water having a NMR half line width using 17O of from about 45 to less than 51 Hz, and an oxide reduction potential of from −1000 to +200 mV, or from +600 to +1300 mV, topical compositions that contain such water, uses for such water to hydrate skin, deliver drugs and treat various skin and mucosal conditions, and methods and apparatus for manufacturing the water.

5 Claims, 6 Drawing Sheets

(56) References Cited

U.S. PATENT DOCUMENTS

| | | | |
|---|---|---|---|
| 5,474,662 | A | 12/1995 | Miyamae |
| 5,507,932 | A | 4/1996 | Robinson |
| 5,510,009 | A | 4/1996 | Arai et al. |
| 5,560,816 | A | 10/1996 | Robinson |
| 5,589,052 | A | 12/1996 | Shimamune et al. |
| 5,593,554 | A | 1/1997 | Yamanaka et al. |
| 5,616,221 | A | 4/1997 | Aoki et al. |
| 5,622,828 | A | 4/1997 | Parma et al. |
| 5,622,848 | A | 4/1997 | Morrow |
| 5,674,537 | A | 10/1997 | Morrow |
| 5,711,950 | A | 1/1998 | Lorenzen |
| 5,731,008 | A | 3/1998 | Morrow |
| 5,759,489 | A | 6/1998 | Miura et al. |
| 5,824,353 | A | 10/1998 | Tsunoda et al. |
| 5,900,127 | A | 5/1999 | Iida et al. |
| 5,965,009 | A | 10/1999 | Shimamune et al. |
| 5,980,703 | A | 11/1999 | Yamada et al. |
| 6,033,678 | A | 3/2000 | Lorenzen |
| 6,093,292 | A | 7/2000 | Akiyama |
| 6,126,796 | A | 10/2000 | Shimamune et al. |
| 6,126,810 | A | 10/2000 | Fricker et al. |
| 6,174,419 | B1 | 1/2001 | Akiyama |
| 6,207,201 | B1 | 3/2001 | Piacenza |
| 6,235,186 | B1 | 5/2001 | Tanaka et al. |
| 6,258,222 | B1 | 7/2001 | Nakamura et al. |
| 6,296,744 | B1 | 10/2001 | Djeiranishvili et al. |
| 6,426,066 | B1 | 7/2002 | Najafi et al. |
| 6,464,845 | B2 | 10/2002 | Shirota et al. |
| 6,527,940 | B1 | 3/2003 | Shimamune et al. |
| 6,632,347 | B1 | 10/2003 | Buckley et al. |
| 7,090,753 | B2 | 8/2006 | Sumita |
| 7,276,255 | B2 | 10/2007 | Selkon |
| 7,291,314 | B2 | 11/2007 | Paskalov et al. |
| 7,303,660 | B2 | 12/2007 | Buckley et al. |
| 7,323,118 | B2 | 1/2008 | Calderon |
| 7,393,522 | B2 | 7/2008 | Najafi et al. |
| 7,442,288 | B2 | 10/2008 | Sumita |
| 2002/0134691 | A1 | 9/2002 | Satoh et al. |
| 2003/0185704 | A1 | 10/2003 | Bernard et al. |
| 2004/0069618 | A1* | 4/2004 | Paskalov et al. ............... 204/193 |
| 2004/0258836 | A1 | 12/2004 | Besenhard |
| 2005/0139808 | A1 | 6/2005 | Alimi |
| 2005/0142157 | A1 | 6/2005 | Alimi |
| 2005/0189237 | A1* | 9/2005 | Sano ............................ 205/746 |
| 2005/0196462 | A1 | 9/2005 | Alimi |
| 2006/0235350 | A1 | 10/2006 | Alimi et al. |
| 2006/0241546 | A1 | 10/2006 | Alimi |
| 2006/0249375 | A1 | 11/2006 | Aoun et al. |
| 2006/0253060 | A1 | 11/2006 | Alimi |
| 2006/0275387 | A1 | 12/2006 | Bagley |
| 2007/0017820 | A1 | 1/2007 | Anderson et al. |
| 2007/0051640 | A1 | 3/2007 | Bellamy |
| 2007/0173755 | A1 | 7/2007 | Alimi et al. |
| 2007/0196357 | A1 | 8/2007 | Alimi et al. |
| 2007/0196434 | A1 | 8/2007 | Alimi et al. |
| 2009/0181107 | A1 | 7/2009 | Buckley et al. |
| 2009/0221989 | A1 | 9/2009 | Najafi et al. |
| 2009/0258083 | A1 | 10/2009 | Calderon |

FOREIGN PATENT DOCUMENTS

| | | | |
|---|---|---|---|
| EP | 1007478 | | 8/2003 |
| EP | 1036861 | B1 | 10/2003 |
| EP | 1600426 | | 11/2005 |
| EP | 1103264 | | 5/2007 |
| EP | 1551770 | | 3/2010 |
| JP | 04235904 | | 8/1992 |
| JP | 06-126287 | * | 5/1994 ............... C02F 1/68 |
| JP | 06126287 | | 5/1994 |
| JP | 11035472 | | 2/1999 |
| JP | 2000229815 | | 8/2000 |
| JP | 2001096272 | | 4/2001 |
| WO | WO97/19707 | | 6/1997 |
| WO | WO2004/078654 | | 9/2004 |
| WO | WO2005/065383 | | 7/2005 |
| WO | WO2007/048772 | | 5/2007 |
| WO | WO2008/091032 | | 7/2008 |
| WO | WO2008/131936 | | 11/2008 |

OTHER PUBLICATIONS

Kiura, H., et. al. "Bactericidal activity of electrolyzed acid water from solution containing sodium chloride at low concentration, in comparison with that at high concentration." J. of Microbiological Methods, 2002, v. 49, p. 285-293.*

Anonymous, "Aquatech Amsterdam 2006 Press Information," [online] Aug. 28, 2006, URL:www.amsterdam.aquatechtrade.com/_upload/aquatech2006/docs/Noviteiten_supplement_ENG.doc.

"BioCera® Alkaline Purifier" [online], URL:http://www.biocera.co.kr/eng/Antioxidant_Alkaline_Water_Filter.htm.

Dermacyn® Wound Care, [online], Oculus Innovative Sciences, URL:www.oculusis.com.

Fenner, Dunja Corinne, "Antimicrobial activity of electrolyzed oxidizing water using standard in-vitro test procedures for the evaluation of chemical disinfectants", [online] Inaugural-Dissertation, Zurich Oct. 6, 2005, URL:http://www.water4u.net/file_download.php?filename=63ff8dbc4bb2121cc20add56549dcbe2.

Hayashi, Hidemitsu, "Benefits of Alkaline, Ionized Water" [online] Oct. 6, 2005, URL:http://www.ionizers.org/water.html.

Hayashi, Hideaki, et al., Artificial Organs, "Successful Treatment of Mediastinitis after Cardiovascular Surgery Using Electrolyzed Strong Acid Aqueous Solution," vol. 21, p. 39-42, 1997.

Hsu, Shun-Yao, et al., Journal of Food Engineering, "Effects of storage conditions on chemical and physical properties of electrolyzed oxidizing water," vol. 65, p. 465-471, 2004.

Kim, Yong Jeong, et al., "Suppression of cobalt dissolution from the $LiCoO_2$ cathodes with various metal-oxide coating", Database Compendex [online] Dec. 2003.

Kim, Tae-Joon, et al., Electrochimica Acta, "Enhanced electrochemical properties of $SnO_2$ anode by $AlPO_4$ coating", vol. 49, No. 25, p. 4405-4410, 2004.

Len, Soo-Voon, et al., J. of Agric. Food Chem., "Effects of Storage Conditions and pH on Chlorine Loss in Electrolyzed Oxidizing (EO) Water," vol. 50, p. 209-212, 2002.

Nakagawara, Shunji, et al., Analytical Sciences, "Spectroscopic Characterization and the pH Dependence of Bactericidal Activity of the Aqueous Chlorine Solution," vol. 14, p. 691-698, 1998.

Venkitanarayana, Kumar S., et al., Applied Enviro. Microbiology, "Efficacy of Electrolyzed Oxidizing Water for Inactivating *Escherichia coli* O157:H7, *Salmonella enteritidis*, and *Listeria monocytogenes*," vol. 65, No. 9, p. 4276-4279, 1999.

Yang, Gordon C.C., et al., J. of Membrane Science, "Reclamation of high quality water from treating CMP wastewater by a novel crossflow electrofiltration/electrodialysis process," vol. 233, p. 151-159, 2004.

International Search Report and Written Opinion for PCT/EP2008/003383 dated Jun. 9, 2009.

International Preliminary Report on Patentability for PCT/EP2006/067676 dated Apr. 29, 2008.

International Preliminary Report on Patentability for PCT/EP2008/003383 dated Oct. 27, 2009.

International Search Report and Written Opinion for PCT/EP2006/067676 dated Jan. 11, 2007.

Hong, Y.J., et al., "Measurement of hydroxyl radical density generated from the atmospheric pressure bioplasma jet," 15th Int. Conf. Laser Aided Plasma Diagnostics (15th LAPD), 2011, in *J. Instrumentation*, 7:C03046 (Mar. 2012).

Voráč, J., et al., "Measurement of hydroxyl radical (OH) concentration in an argon RF plasma jet by laser-induced fluorescence," *Plasma Sources Sci. Technol.*, 22:025016 (9 pp.) (2013).

Brown and Gu, "The chemistry of perchlorate in the environment," Chapter 2 in *Perchlorate: Environmental Occurrence, Interactions and Treatment*, B. Gu and J.D. Coates, Eds. (Springer, 2006), p. 17-47.

Liao, L.B. et al., "The generation and inactivation mechanism of oxidation-reduction potential of electrolyzed oxidizing water," *J. Food Engineering*, 78:1326-1332 (2007).

* cited by examiner

HIGHLY STABLE ELECTROLYTIC WATER WITH REDUCED NMR HALF LINE WIDTH

RELATIONSHIP TO PRIOR APPLICATIONS

This application claims priority to U.S. Provisional Application No. 60/926,182, filed Apr. 25, 2007. The contents of said application are incorporated by reference as if fully set forth herein.

TECHNICAL FIELD

The present invention relates to highly stable alkaline and acid waters produced by electrolysis, to methods for making and using the alkaline and acid waters, and to devices for making the waters of the present invention.

BACKGROUND ART

It is known that aqueous solutions of salts, particularly sodium chloride, as a consequence of an electrolytic treatment, are split into two liquid products, one having basic and reducing characteristics (generally known as cathode water or alkaline water) and another (generally known as anode water or acid water) having acid and oxidizing characteristics.

Conventional electrolytic waters suffer the acknowledged drawback of having very limited preservation. A few days after preparation, the product in fact generally tends to degrade and lose its properties. Known electrolytic waters, therefore, must be prepared and used substantially on the spot. Accordingly, the commercial utilization of the product in itself is extremely disadvantageous, since the shelf life of any ready-made packages is dramatically limited.

Several companies manufacture alkaline water for drinking purposes, and tout the water based upon its antioxidant characteristics. These waters are made by numerous processes, on industrial and single-home scales, by processes including electrolysis and ultrasound. In general these waters have a pH not far from neutral, generally no greater than 9 or 10. The waters of the present invention are not intended for consumption, and generally have a much higher pH than manufactured drinking waters.

The band width in an $^{17}O$—NMR spectrum of water, taken half way along the amplitude of the water's peak (the "NMR half line width") (also known as the "full width at half height" or "FWHH"), is reportedly 80 Hz or more for tap water obtained from underground water, and about 120 Hz for tap water obtained by purifying river water or ordinary waste water (a journal, "Shokuhin To Kaihatsu", Vol. 24, No. 7, 1991, p. 83). U.S. Pat. No. 5,824,353 reports water having an $^{17}O$—NMR half line width of less than 50 Hz. The water is produced by ultrasonic vibration, and depends on the presence of specific concentrations of potassium, magnesium and calcium ions for its stability and small NMR half line width.

OBJECTS OF THE INVENTION

One object of the present invention is to provide electrolytic alkaline and acid waters which overcome the drawbacks of the background art. Within this aim, one of the objects of the present invention is to provide electrolytic alkaline and acid waters that have high stability over time, a low production cost and easy preparation.

Another object of the present invention is to provide pharmaceutical and cosmetic compositions that are capable of imparting improved skin hydration, or delivering active pharmaceutical ingredients, preferably using the alkaline water of the present invention.

Another object of the invention is to provide an electrolytic water as defined above which has a high capacity for penetration into mammalian tissues, such as the deep layers of the skin and, and that can treat or prevent various skin disorders and pathologies.

Still other objects of the present invention are to provide methods for preparing the electrolytic alkaline and acid waters of the present invention, and devices and apparatuses that can be used for preparing electrolytic alkaline and acid waters of the present invention.

SUMMARY OF THE INVENTION

These and other aims and objects are achieved by an electrolysis process that employs special nano-coated electrodes in anode and cathode chambers, and a special nano-coated membrane between the anode and cathode chambers, to produce electrolytic alkaline and acid waters that are essentially free from heavy metals, and that have an $^{17}O$ NMR half line width that is much lower than electrolytic water produced in the prior art, on the order of 45-51 Hz. The NMR half line width is a direct reflection of the quality and consistency of the water produced by the methods of the current invention, since it varies depending on the mean cluster size and distribution of molecular cluster sizes in the water.

Therefore, in one embodiment, the invention provides electrolytic acid or alkaline water having a NMR half line width using $^{17}O$ of from about 45 to less than 51 Hz, and an oxide reduction potential of from −900 to +200 mV, or from +600 to +1300 mV. In a more preferred embodiment, the alkaline waters of the present invention are characterized by an oxide reduction potential of from about −900 to about −200 mV, a pH of from about 8.5 to about 13.0, and/or an absence of any detectable heavy metals. The acid waters of the present invention are preferably characterized by an oxide reduction potential of from about +1000 to abut +1300 mV, a pH of from about 1.0 to about 3.0, and/or an absence of any detectable heavy metals. In a particularly preferred embodiment the water has a stability, in terms of pH, ORP or NMR half line width, that exceeds 30, 90, 180 or even 365 days, when stored under appropriate conditions that shield the product from light, air and heat.

In another embodiment the invention provides for topical compositions that include the alkaline and acid waters of the present invention. In particular, the invention provides a topical composition comprising as ingredients an electrolytic acid or alkaline water having a NMR half line width using $^{17}O$ of from about 45 to less than 51 Hz; and one or more cosmetically or pharmaceutically acceptable topical excipients.

In another embodiment the invention provides an electrolysis unit, and a method of using such unit for making electrolytic acid or alkaline water having a NMR half line width using $^{17}O$ of from about 45 to less than 51 Hz, comprising:

(a) providing an electrolysis unit comprising: (i) a cathode chamber, an anode chamber, and a filter separating said chambers (preferably characterized by a porosity that allows ionized fractions of nano-clustered $H_2O$ to pass, such as when the porosity is predominantly characterized by pores of from about 120 to about 180 nm in diameter (preferably having a mean diameter between 120 and 180 nm)); and (ii) a cathode situated in said cathode chamber and an anode situated within said anode chamber, wherein at least one of said anode and cathode is coated by a residue of particles in which greater than 70% by weight of said particles have a diameter of from 40 to 100 nm;

(b) introducing a solution of water and an alkaline earth metal salt into one or both of said chambers; and (c) applying an electric potential to said anode and said cathode, for a time and to an extent sufficient to produce electrolyzed alkaline or acidic water having a NMR half line width using $^{17}O$ of from about 45 to less than 51 Hz.

Other embodiments relate to specific uses for the alkaline and acid water fractions of the electrolytic water of the present invention, particularly in the medical and cosmetic arts. In one embodiment the water is used as a skin hydrating agent either by itself or as part of a topical cosmetic or pharmaceutical composition, or for assisting the delivery of one or more pharmaceutical agents. The water is also useful in the treatment or prevention of superficial or deep disorders or lesions of the skin or dermis or mucosa, including sores, inflammatory disorders, infections, burns and abrasions. The acid water has been found to be particularly useful in the treatment of skin and mucosal lesions, because of its curative effects on skin and mucosa, and its ability to promote collagen production and other metabolic processes necessary for skin and mucosal healing.

The aim and objects of the invention are also achieved by a composition which comprises an acid or alkaline water as defined above and one or more ingredients (preferably viscosity increasing agents) selected from the group that consists of:

i) excipients and carriers which are pharmaceutically acceptable for preparing pharmaceutical compositions for human or animal use, ii) excipients and carriers which are cosmetically acceptable for preparing cosmetic compositions for human or animal use, iii) excipients and carriers used in the food sector to prepare disinfectant compositions, and iv) excipients and carriers used in the agricultural sector to prepare antiparasitic or fungicide compositions.

The aims and objects of the invention are also achieved by a kit which comprises an electrolytic alkaline or acid water as defined herein and means for applying it to a substrate, such as a dispensing container, a wipe or a bandage.

The aim and objects of the invention are also achieved by the use of an alkaline or acid water as defined above to prepare a medication for treating and preventing superficial or deep skin and mucosa disorders or lesions of the human or animal body.

The aim and objects of the invention are also achieved by the use of an electrolytic alkaline or acid water as defined above to sanitize a substrate.

The aim and objects of the invention are also achieved by the use of an electrolytic alkaline water or acid water as defined above to provide a solution for over-oxidation of the human or animal body.

The aim and objects of the invention are also achieved by the use of an alkaline or acid water as defined above for cosmetic treatment of the human or animal body or of isolated parts thereof, especially as a topical anti-aging product, or to dispel black sedimentation on the skin from oxidation processes.

The aim and objects of the invention are also achieved by the use of an alkaline water or acid water as defined above to carry preparations suitable for bone reconstruction.

The aim and objects of the invention are also achieved by the use of an electrolytic alkaline water or acid water as defined above to rehydrate dehydrated human or animal tissues for reimplantation.

Additional embodiments and advantages of the invention will be set forth in part in the description which follows, and in part will be obvious from the description, or may be learned by practice of the invention. The embodiments and advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

WAYS OF CARRYING OUT THE INVENTION

Figure 1:
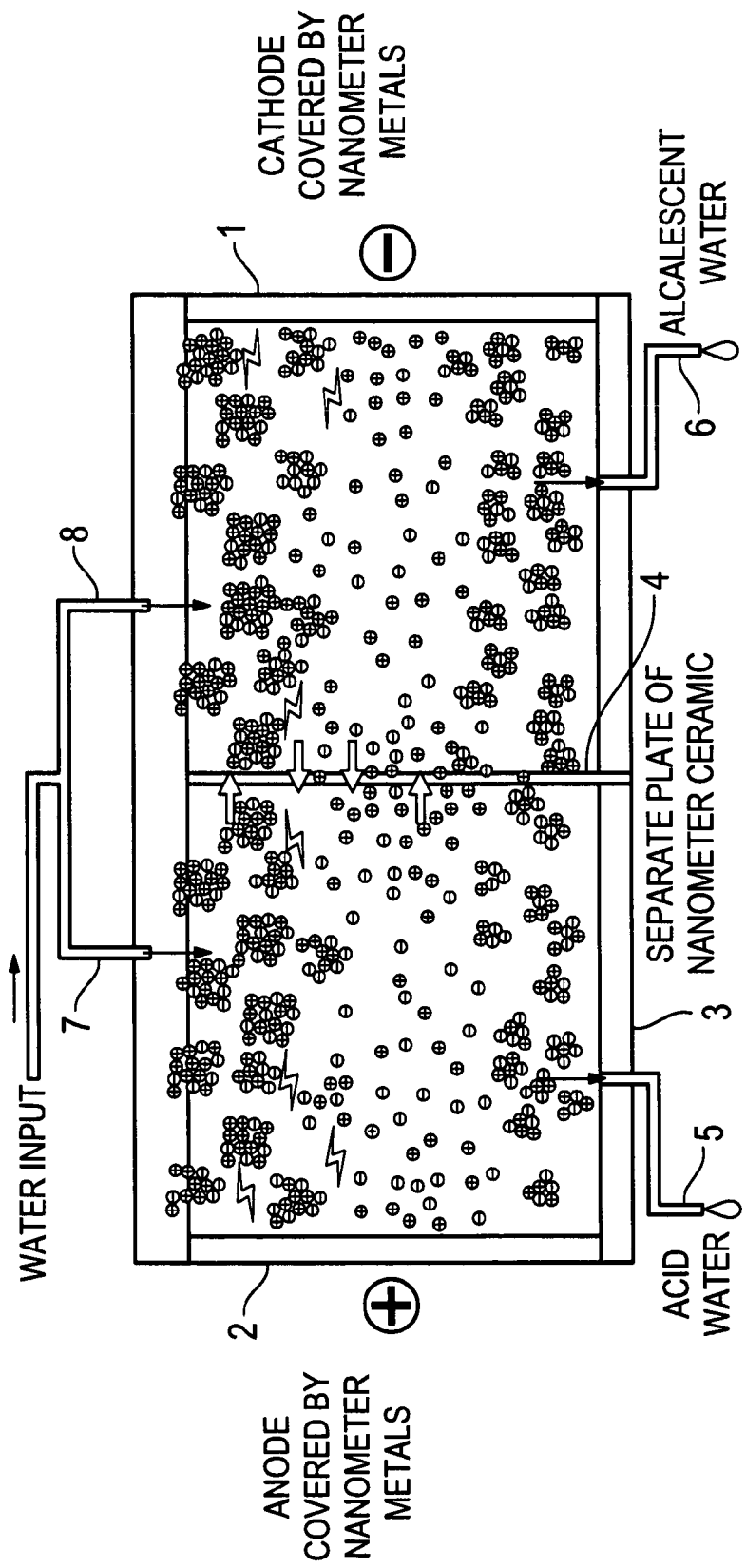
FIG. 1 is a schematic view of the electrolytic device 1 according to the invention, which comprises an electrolysis chamber 2 and two electrodes 3 and 4.

The present invention may be understood more readily by reference to the following detailed description of preferred embodiments of the invention and the Examples included therein.

Definitions and Use of Terms

The term "fluid" is used to reference any pure fluid, solution or suspension which is capable of producing a non-spontaneous chemical reaction if subjected to electrolysis. One highly preferred fluid is water. The term "water" is used to reference any type of water, such as tap water, filtered water, deionized water, and distilled water. A water which can be treated with the invention can have a higher percentage of solid pollutants in solution than waters which can be treated with conventional devices, by virtue of the possibility to provide a continuous reversal of polarity between the electrodes (polarity swapping, as defined below). Any polluting solutes, if electrically charged, would in fact be attracted by the opposite pole, forming a flow which would rapidly clog the pores of any membrane provided in the electrolytic device, blocking the process. On the contrary, continuous and rapid reversal of polarity does not produce any flow and the pores of the membrane, if provided, remain clean and efficient. Once subjected to electrolysis, the water separates into two liquid fractions, which for the sake of simplicity are referenced here as acid water or anode water and as cathode water or alkaline water.

Electrolytic water means water produced by the process of electrolysis, and is preferably characterized by an oxide reduction potential (ORP) and/or pH that reflects its acid or alkaline nature. The ORP of electrolytic alkaline water preferably ranges from −1000 to +200 or 0 mV, −900 to −200 mV, or −900 to −600 mV. The pH of electrolytic alkaline water preferably ranges from 8.0 to 13.0, 8.5 to 12.5, or 10 to 12. Alternatively, the pH of the alkaline water may range from 11.0 to 13.0 or from 11.5 to 13.0.

The ORP of electrolytic acid water preferably ranges from +600 to +1350 mV, more preferably from +800, +900, or +1000 mV to +1300 mV, most preferably from +1100 to +1250 mV. The pH of the acid water preferably ranges from 0.5 or 1.0 to 6.0, 5.0, 4.0, or 3.0, and most preferably ranges from 1.0 to 3.0.

As used in this specification and in the claims which follow, the singular forms "a," "an" and "the" include plural referents unless the context clearly dictates otherwise. Thus, for example, reference to "an ingredient" includes mixtures of ingredients, reference to "an active pharmaceutical agent" includes more than one active pharmaceutical agent, and the like.

When used herein, the term skin is used in its ordinary sense, and includes the epidermis or outer layer of the skin, the dermis or middle layer of the skin, and the subcutaneous or deepest layer of the skin. When reference is made to penetration through the skin, treatments of the skin, and disorders or lesions of the skin, it will be understood that all three layers of the skin are intended, and that each layer constitutes a separate embodiment for purposes of this invention. It will further be understood that disorders of the skin include disorders of skin components such as nails and hair. When the term "skin or dermis," is employed it is not intended to impart a different meaning to skin; rather, it is simply meant to emphasize the ability of the waters of the present invention to penetrate and influence deep skin pathologies.

"Treating" or "treatment" of a disease includes (1) preventing the disease from occurring in an animal that may be predisposed to the disease but does not yet experience or display symptoms of the disease, (2) inhibiting the disease, i.e. arresting its development, or (3) relieving the disease, i.e. causing regression of the disease.

The terms "sanitize", "sanitization" or "sanitizing" in the invention reference the provision of a combined effect of disinfection, sanitization and cleaning. In particular, the disinfection effect comprises a bactericidal, fungicide, sporicidal and virucidal effect.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Cosmetically acceptable" means that which is useful in preparing a cosmetic composition that is generally safe, non-toxic and neither biologically nor otherwise undesirable and includes that which is acceptable for human cosmetic use.

"Therapeutically effective amount" means that amount which, when administered to an animal for treating a disease, is sufficient to effect such treatment for the disease. When a pharmaceutically active agent is administered in accordance with this invention it will be administered in a therapeutically effective amount.

When ranges are given by specifying the lower end of a range separately from the upper end of the range, it will be understood that the range can be defined by selectively combining any one of the lower end variables with any one of the upper end variables that is mathematically possible.

The characteristics and advantages of the present invention in all of its aspects are now described exclusively in relation to the highly preferred embodiment in which the fluid to be subjected to electrolysis is water. However, on the basis of the information and details provided hereinafter, it will be immediately evident to the person skilled in the art that it is possible to achieve the same advantages also with the electrolysis of fluids other than water.

Electrode Construction

With reference to FIG. 1, it can be seen that the invention relates partly to an electrode (i.e. a cathode 1 or anode 2), particularly for electrolytic cells, characterized in that it comprises a surface coating which comprises nano-particles of one or more metals. In a preferred embodiment, the electrode comprises a core which is made of a metallic material, a nonmetallic material or combinations thereof.

If the core is made of metallic material, it can be made for example of an alloy of titanium and platinum or an alloy of steel and graphite. If the core is made of a nonmetallic material, it can be made for example of graphite. The core may also comprise different layers, such as for example a core made of graphite which is coated with an outer layer of metal, for example titanium. The term "metal" references both a metal and chemical compounds which comprise said metal, such as its oxides. A preferred core is made of $TiO_2$.

The electrode according to the invention is characterized with respect to known electrodes substantially due to the presence of a nanometer covering (hereinafter also referenced as coating) which is extremely smooth, i.e., a layer for covering the core which includes metallic nano-particles.

The metals of which the nano-particles of the coating are made are selected preferably among one or more of titanium, iridium, yttrium, ruthenium, zinc, zirconium platinum, selenium, tantalum and compounds thereof. Preferred metal compounds are oxides of the mentioned metals. A preferred coating comprises $ZrO_2$, $ZnO$, $Ru_2O_3$, $IrO_2$ and $Y_2O_3$, or $TiO_2$, $Pt/ZrO_2$, $SnO_2$, $Ta_2O5$, and $IrO_2$. Preferably, the various metals are used in powder form.

In one embodiment, the coating can also comprise a nonmetallic carrier material, for example particles of one or more polymers. The polymer can be synthetic (such as for example plastics, acrylic polymers, et cetera) or partly synthetic (such as for example modified celluloses, modified starches, et cetera). The metallic nano-particles comprised within the coating are preferably used in powder form. As regards the size distribution within the powder, preferably an amount at least equal to 70%, 75%, or 80% by weight of the particles that are present in the powder, more preferably at least equal to 85%, has a particle diameter ranging from 40 to 100 nm, 50 to 90 nm, or 60 to 80 nm.

In another aspect, the invention relates to a method for obtaining an electrode. The coating can be provided by means of nanotechnology techniques which are known to a person skilled in the art and are adapted to produce a smooth surface, for example by sintering the powder or the mixtures of metallic nano-powders.

The individual metals in powder form can be applied to the electrode so as to produce the coating: 1) as a preformed mixture, and/or 2) in the form of discrete layers which are applied sequentially and mutually superimposed and wherein each layer consists of a single metal, and/or 3) in the form of discrete layers which are applied sequentially and mutually superimposed and in which each layer consists of two or more metals but not simultaneously of all the metals that are present in the coating.

In a preferred embodiment, the method comprises the step (A) of preparing the coating of the electrode by sintering powders of nano-particles of one or more metals as defined above directly on the core of the electrode. Preferably, step (A) comprises the following steps to be performed in the order in which they are listed here:

(A1) preparing one or more powders of metallic nano-particles as defined above, (A2) dissolving the one or more powders of nano-particles in a suitable solvent and in at least such a quantity as to be able to dissolve all the powder to be applied, obtaining one or more solutions, and (A3) sintering the one or more solutions obtained in the preceding step on a metal plate, preferably passivated on its surface, which will form the core of the electrode.

Preferably:

the one or more powders of metallic nano-particles of step (A1) is a combination of powders of $ZrO_2$, ZnO, $Ru_2O_3$, $IrO_2$ and $Y_2O_3$, or $TiO_2$, $Pt/ZrO_2$, $SnO_2$, $Ta_2O5$, and $IrO_2$, advantageously obtained by hydrothermal chemical processing, at least 70%, 75%, or 80% and more preferably at least 85% by weight of the particles in the powder have a diameter ranging from 60 to 80 nm;

the solvent of step (A2) in which each powder is dissolved is preferably a 30% solution by weight of hydrochloric acid in water, in at least such an amount as to be able to dissolve all the powder to be applied, step (A3) consists in sintering the aqueous solutions of hydrochloric acid obtained from step A(2) on both faces of a $TiO_2$ plate which is passivated on its surface and has a thickness ranging from 0.15 to 0.35 mm, wherein sintering may occur according to the following steps:

| Step | Solution | Dosage per unit surface | Sintering time(min) | Sintering temperature(° C.) |
|---|---|---|---|---|
| 1 | $IrO_2$ | 0.2 g/m$^2$ | 45 | 450 |
| 2 | $Ru_2O_3$ | 0.2 g/m$^2$ | 45 | 450 |
| 3 | ZnO + $Y_2O_3$ (Y at 2 mol) | 0.15 g/m | 60 | 550 |
| 4 | $IrO_2$ | 0.25 g/m$^2$ | 45 | 450 |
| 5 | $Ru_2O_3$ | 0.25 g/m$^2$ | 60 | 550 |
| 6 | $ZrO_2$ + $Y_2O_3$ (Y at 3 mol) | 0.1 g/m$^2$ | 60 | 550 |
| 7 | $Ru_2O_3$ | 0.15 g/m$^2$ | 60 | 550 |
| 8 | $IrO_2$ | 0.15 g/m$^2$ | 60 | 550 |
| 9 | $IrO_2$ + $Ru_2O_3$ | 0.15 g/m$^2$ + 0.15 g/m$^2$ | 60 | 600 |
| 10 | $ZrO_2$ + $Y_2O_3$ (Y at 3 mol) | 0.1 g/m | 60 | 600 |
| 11 | $IrO_2$ + $Ru_2O_3$ | 0.15 g/m$^2$ + 0.15 g/m$^2$ | 60 | 600 |

Resorting to multiple sintering steps has been found to be particularly useful in order to eliminate any roughness from the surface of the electrode and obtain an extremely hard and smooth surface. An electrode as defined above, used as part of a device for providing the electrolysis of water, produces the following advantages:

more efficient electrolysis, in that there is a lower consumption of salts such as NaCl, used conventionally to accelerate the electrolysis of low-conductivity fluids such as water; and in the highly preferred embodiment in which both electrodes are electrodes according to the invention, the possibility to provide a continuous change of polarity of the electrodes ("polarity swapping"). The sudden change of polarity allows the charged particles that are present in the fluid subjected to electrolysis to circulate in both directions instead of just in one (forced by the charge of the particles and by the unchangeable sign of the electrodes), thus avoiding the forming of deposit-producing masses at the level of the electrodes and thus keeping their surface clean and their efficiency at the maximum level. Moreover, if a semipermeable membrane is provided within the electrolytic cell and divides the two anode and cathode half-chambers, the change of polarity avoids the clogging of the pores of said membrane, extending the life of the device;

the presence of a nanometer coating determines an accumulation of charge by the upper electrode to more than 100% with respect to conventional electrodes. This allows to provide a qualitatively and quantitatively different electrolysis at significantly higher potentials, with the effect of, for example, reducing the size of molecular clusters;

the obtainment of a very high consistency, smoothness and surface density, aspects which avoid the solubilization of the electrode itself or the forming of sediments on its surface, which would then occur in the acid and alkaline water fractions. The same aspects are also the basis for the substantially nil release of heavy metals and other compounds which constitute the surface and core of the electrode within the acid and alkaline water fractions. As will be mentioned also hereafter, the absence of heavy metals in the alkaline water leads to an amazing stability thereof over time, with preservation of characteristics such as ORP, pH and molecular cluster size. This stability is unknown to known equivalent products. The same aspects are also the basis for the minimal maintenance required by the electrode, which can be changed with a significantly lower frequency than known electrodes, reducing costs and increasing ease of production;

the possibility to obtain quantum effects (known in the literature also by the term "nano-effects") by means of the nanometer dimensions of the coating particles. Briefly, when nanometer dimensions are reached, the optical, magnetic and electrical properties of matter change radically. By reducing the dimensions until the typical nanometer dimensions of so-called clusters are reached, due to the small number of atoms that are present in said cluster and to its reduced volume, a discretization of the energy levels (quantization) becomes apparent in the electron structure and depends on the size of the cluster, this phenomenon is known as "quantum size effect" and entirely new characteristics, which contrast with the ones that are typical of the material at ordinary dimensions, depend from it. In the present case, the best performance has been obtained with powders which have a size distribution centered in an interval ranging from 60 to 80 nm as indicated above. As a whole, the effects described above produce the simultaneous presence of three factors which are a key aspect of the invention: stability of the resulting alkaline water, ease of its production (for example thanks to the lower maintenance costs and to the greater durability of the device as a whole) and an increase in its quality (especially in terms of purity and constancy of properties over time). In particular, the increase in the quality of the alkaline water can be measured both in terms of uniformity of the dimensions of the molecular clusters (higher percentage of micromolecules with respect to the number of macromolecular clusters) and in terms of increased stability over time of the properties given to the water by the electrolysis itself (above all alkalinity, ORP and cluster size). The stability increase presumably achieves the preservation over time of the structural surface characteristics of the electrodes coated with a nano-coating as described here.

Electrolysis Chamber and Operation Thereof

The embodiment in which the device comprises a single electrolysis chamber 3 divided into two portions by a membrane 4, and a single pair of electrodes 1 and 2 within said chamber is described hereinafter. However, the person skilled in the art will know how to adapt the description to other embodiments which comprise more than one electrolysis chamber and more than one pair of the electrodes. The number of chambers can be changed, for example, in order to achieve higher treatment speeds or flow-rates of water in output.

In a highly preferred embodiment, both electrodes of the device are nano-coated electrodes as defined above. However, the advantages in terms of low cost and efficiency of the electrolysis process, as well as the advantages in terms of stability over time of alkaline water, can be obtained also if only one of the two electrodes is nano-coated as defined above.

Preferably, the device according to the invention also comprises a membrane 4 adapted to divide the at least one chamber into two half-chambers, wherein the half-chamber that contains the anode is termed an anode half-chamber, and the half-chamber that contains the cathode is termed a cathode half-chamber. The membrane is advantageously an ultrafiltration membrane which can occupy the chamber partially or totally.

The membrane 4 can be of the type used in conventional electrolytic cells, but is preferably based on size exclusion technology at the nano-scale. In a particularly advantageous embodiment the membrane is made of ceramic material with open porosity, coated with metallic nano-particles, preferably nano-particles of oxides of zirconium, yttrium, aluminum or mixtures thereof. The metallic nano-particles used to make the coating are preferably in powder form. As regards the size distribution within the powder, preferably an amount at least equal to 70%, 75%, or 80% by weight of the particles that are present in the powder, more preferably at least equal to 85%, has a particle diameter ranging from 30 to 100 nm, 40 to 70 nm, or 50 to 60 nm.

By resorting to nanometer particles to manufacture the membrane 4, the average pore size of the final membrane has been found to be extremely constant over time and adaptable according to the requirements of how the water is to be processed. In a preferred embodiment, the average pore size is from about 120 to about 180 nm (mean or median). Size constancy over time and constancy of the pore dimensions themselves are two aspects which differentiate the ceramic membrane described here from the textile membranes conventionally used in equivalent devices (which are instead subject to rapid deterioration over time). In a preferred embodiment, at least 50%, 70%, 90%, 95%, 98% or 99% of the pores have a diameter between 120 and 180 nm. These aspects have shown a positive effect on the stability of the alkaline water obtained after electrolysis, where this effect combines with, and augments, the stabilizing effect produced by the use of an electrode as defined above.

In a particularly advantageous embodiment, each half-chamber is connected to the outside of the device through:

openings 7 and 8 arranged in the upper part of the half-chamber from which the water to be subjected to electrolysis is inserted, and additional openings 5 and 6 arranged in the lower part of the half-chamber which can act as a discharge for the resulting acid and alkaline fractions (referenced as "acid water" and "alkalescent water" in FIG. 1). The second opening on the lower part of each half chamber is provided with closure means (not shown) which is adapted to prevent the water that has not yet separated from leaving the half-chamber and are adapted to be opened at the end of the electrolytic process.

With specific reference to FIG. 1, the operating mechanism of a device as described above provided with all the essential and optional elements that have been listed, therefore entails treating water by introducing it from above, by means of the water input ducts, into the two half-chambers of the main chamber. Here, the water, under the action of the cathode and of the anode previously connected to the negative and positive poles of an electric voltage source, is split into positive and negative ions, which, as is known, are attracted by the respective opposite poles. In passing from one half-chamber to the other, the nano-porous membrane acts as a filter for said ions and for any charged particles, allowing only the particles of sufficiently small size to pass.

In a preferred embodiment the water input to the unit is characterized by its conductivity, preferably measured in $\mu S/cm$. Thus, for example, the water can be described by the consistency of conductivity in the water input. For example, the conductivity should vary by no more than 50, 20, 10, 5 or even 2 $\mu S/cm$, or 100, 50, 20 or 10%. The water may also be described by the conductivity of the water itself. Thus, in various embodiments, the conductivity ranges from 0.5, 1.0 or 1.5 $\mu S/cm$ to 50, 25, 10, 5 or even 3 $\mu S/cm$, based on any selection of endpoints. In preferred embodiments the conductivity ranges from 1 to 10 or 1 to 3 $\mu S/cm$, and in a most preferred embodiment the conductivity is about 2 $\mu S/cm$. It has been discovered that by controlling the consistency of the conductivity, and by lowering the conductivity to the preferred values, one is able to obtain much more consistent quality electrolyzed water, with a consequent reduction in NMR half line width. A preferred type of water due to its constant conductivity is osmotic water prepared by reverse osmosis.

Also of importance, the filter prevents the transmission of heavy metals from one chamber to the other. Thus, by introducing the water into the acidic or alkaline chamber, one is able to produce alkaline or acid water having practically no contamination by metallic radicals (or at least beyond the limits of detection).

Characterization of Alkaline and Acid Waters

In another aspect, the present invention relates to an electrolytic alkaline or acid water which can be obtained with a water electrolysis method as defined above. The electrolytic alkaline and acid waters according to the present invention differ from known similar products substantially in their stability, which is due to the higher performance of the nano-coated electrodes and the electrolysis process. In conventional processes, even when the water is subjected to a filtration step before electrolysis, the electrodes tend to break up on their surface during the process, releasing large amounts of heavy metals (particularly of the metal or metals of which the cathode and anode are made).

The alkaline and acid waters according to the invention are instead free from heavy metals in that said metals, if present, are present in a quantity which is below the limits that can be detected with ordinary analytical methods. For example, the alkaline water according to the invention has a cadmium concentration of less than 5 µg/l, less than 10 µg/l of chromium, less than 5 µg/l of lead, and less than 20 µg/l of nickel. Suitable test methods for these heavy metals are described in Table 1 below:

TABLE 1

| Test | Testing method |
|---|---|
| CADMIUM | APAT CNR IRSA 3120/2003 |
| TOTAL CHROMIUM | APAT CNR IRSA 3150/2003 |
| LEAD | APAT CNR IRSA 3230/2003 |
| NICKEL | APAT CNR IRSA 3220/2003 |
| FIXED RESIDUE AT 180° C. | APAT CNR IRSA 2090A/2003 |

Although one does not intend to be bound to any particular theory, it is believed that the absence of heavy metals is one of the main reasons for the unusual and advantageous stability over time of the electrolytic alkaline and acid waters obtained with the present invention. The expression "stability over time" is used to mean that the alkaline water of the present invention, if kept sheltered from the light, air and heat, keeps its chemical and physical properties, particularly its pH, ORP and/or NMR half line width, substantially unchanged for greater than 60 or 90 days, preferably greater than 180 days, even more preferably greater than 365 days. By substantially unchanged, it is meant that the property under evaluation does not vary by more than 50, 30, 15, 10, 5, or even 3% during the applicable time frame.

In like manner, the topical compositions in which the alkaline or alkaline water may be integrated benefit from an improved stability, particularly as measured by pH and/or viscosity. These physical properties preferably remain substantially unchanged in these formulations for greater than 60 or 90 days, preferably greater than 180 days, even more preferably greater than 365 days. By substantially unchanged, it is meant that the viscosity or pH does not vary by more than 50, 30, 15, 10, 5, or even 3% during the applicable time frame.

Although the stability time depends on the steps taken to preserve the solution, it must be noted that for equal storage conditions, an acidic water obtained by using an electrolytic device as defined above has shown a distinctly higher stability than known similar products, which in the best cases have shown a shelf life of only 60-90 days. Therefore, these products must be obtained and used over a short period or even simultaneously with their production. Therefore, the electrolytic acidic water according to the invention can be useful also for applications in locations (Third World countries) and situations (scarcity of water to provide electrolysis) in which, although it is necessary to have for example a valid disinfectant, favorable conditions for its production are not available.

In a preferred embodiment, the electrolytic alkaline water according to the invention has a pH which is advantageously equal to, or higher than, 8.5, 9.0, 10.0, 10.5, 11.0 or 11.5, and equal to or less than 13.5, 13.0 or 12.5 most preferably ranging from 8.5 to 13.0 or 10.0 to 12.5. Alternative pH ranges for the alkaline water are from 11.0 to 13.0 or 11.5 to 13.0. The water preferably has an ORP (oxide reduction potential) when initially produced of from −200 mV to −900 or −1000 mV, and preferably from −600 mV to −900 mV. When the water is processed before it is introduced into a formulation it is typically exposed to air, which typically increases the ORP to a range varying from 0, +100, or +200 mV to +500, +400 or +350 mV. The pH typically is not altered until the water is mixed into a formulation.

The ORP of electrolytic acid water preferably ranges from +600 to +1350 mV, more preferably from +800, +900, 1000 or +1100 mV to +1300, 1250 or +1200 mV, most preferably from +1100 to +1250 mV. The pH of the acid water preferably ranges from 0.5 or 1.0 to 6.0, 5.0, 4.0, or 3.0, and most preferably ranges from 1.0 to 3.0.

Nuclear magnetic resonance $^{17}O$ NMR measures, particularly when evaluated at the half way point of the water peak, is useful to measure the quality of acid and alkaline waters of the current invention, because it reflects intrinsic properties of the water structure such as the median molecular cluster size of $H_2O$ molecules, and the distribution of molecular cluster sizes, in addition to contaminants such as ionic species within the water. The expression "molecular cluster" designates the number of molecules of water which are coordinated in an ordered structure. Nuclear magnetic resonance $^{17}O$ NMR testing of the alkaline waters of the present invention shows that the frequency width halfway up the peak (i.e. the "$^{17}O$ NMR half line width") of an alkaline water according to the invention is 45-55 Hz, while for known products it is 110-130 Hz.

In most preferred embodiments, the $^{17}O$ NMR half line width for alkaline and acid water is equal to or greater than 45, 46, or 47, and less than 51, 50 or 49 Hz, wherein the range can be selected from any of the foregoing endpoints. Thus, for example, in preferred embodiment, the alkaline or acid water of the present invention has an NMR half line width ranging from 45 to less than 51 Hz, or 45 to less than 50 Hz, or 46 to less than 50 Hz.

The acid water may also be characterized by the presence and quantity of chlorine species in the water. One of the following assays or any combination of the following assays may be used to characterize the water. According to the free chlorine assay (spectrophotometric method), or the total chlorine assay (spectrophotometric method), the water may be defined as containing less than 70, 60, 55, 52 or even 50 mg/l of chlorine species. According to the total chlorine assay (iodometric method), the water may be defined as containing less than 80, 70, 65, or even 62 mg/l of chlorine species. According to the UNI 24012 (Mercurimetric method) chloride assay, the water may contain greater than 130, 150 or even 170 mg/l of chloride. Chlorites (as $ClO_2$—), when measured by EPA 300.1 (1997) (detection limit 100 ug/l), are preferably non-detectable. Chlorates ($ClO_3$—), when measured by EPA 300.1 (1997) (detection limit 0.1 mg/l), are preferably present in an amount less than 10, 5, 2, or even 1 mg/l.

In yet another embodiment the acid water may be characterized by a combination of assays, in which free chlorine measured spectrophotometrically is present at less than 10 or 5 or 2 mg/l, total chlorine measured spectrophotometrically is present at less than 10 or 5 or 3 mg/l, and total chlorine measured iodometrically ranges from 100, 200 or 250 mg/l to 500, 400, or 350 mg/l.

Although in certain embodiments the alkaline water may contain oxidizing chlorine species in amounts of up to 60 or even 100 mg/l, in a preferred embodiment the alkaline water according to the invention is essentially free of oxidizing chlorine species, or other anionic residues of salts that are generated during the electrolytic process, i.e. less than 10 or even 5 mg/l, and preferably undetectable.

Uses for Acid and Alkaline Waters

In another aspect, the present invention relates to a composition particularly for sanitizing a substrate which comprises an alkaline or acid water as defined above and one or more ingredients selected from the group that comprises (preferably viscosity increasing ingredients):

i) excipients and carriers which are pharmaceutically acceptable for preparing pharmaceutical compositions for human or animal use, ii) excipients and carriers which are cosmetically acceptable for preparing cosmetic compositions for human or animal use, iii) excipients and carriers used to prepare disinfectant compositions, and iv) excipients and carriers used in the agricultural sector to prepare antiparasitic or fungicide compositions.

It should also be noted that the fixed residue of an electrolytic alkaline or acid water is distinctly lower than the fixed residue of any other differently obtained disinfectant composition. Therefore, thanks to its stability, the acidic water according to the invention can be used for example in all those disinfectant sectors, such as cleaning and maintaining the hygiene of contact lenses, in which one wishes to combine a high but prolonged disinfectant power with the need to not leave deposits or residues on the treated surfaces. Currently, the use of electrolytic acidic waters for this purpose is prevented by the limited stability over time of the disinfectant power.

In another aspect, the present invention relates to a kit which comprises an electrolytic alkaline or acid water as defined above or a composition which comprises said water and means for applying it to a substrate, such as a container dispenser system, a gauze or a bandage. The substrate is advantageously selected among 1) inanimate objects and surfaces, 2) the human or animal body, and 3) isolated parts of the human or animal body. Examples of the three classes mentioned above are provided below with reference to the aspect of the sanitizing use of an alkaline or acid water as defined above.

Some additional applications of an alkaline or acid water according to the invention are described hereinafter and are allowed by the particular properties thereof and especially by the combination now obtainable of easy production at very low costs, stability of the resulting water and purity thereof. For example, the present invention also provides for the use of an electrolytic alkaline or acid water as defined herein in a composition for hydrating the skin, or for delivering an active pharmaceutical ingredient to or through the skin or mucosa. Dosage forms in which the water can be integrated include transdermal patches, gels, creams, ointments, topical washes and the like. When used to deliver pharmaceuticals, the pharmaceutical agent to be delivered can be a locally acting agent, such as a topical anesthetic or topical antimicrobial, or the pharmaceutical agent may be a systemically acting agent which must penetrate the skin and enter the bloodstream to exert its therapeutic effect. When the water is used as a hydrating agent, the hydrating composition preferably omits penetration accelerators that disrupt the skin's barrier mechanisms.

Alternatively, the composition can be developed as a medication for treating and preventing superficial or deep skin or mucosa disorders or lesions of the human or animal body. The use to prepare a medication, exactly like all of the aspects of use discussed below, is described with explicit reference to the use of an alkaline or acid water according to the invention. However, it will be immediately evident to the person skilled in the art that the same advantages in terms of use can be achieved by using not the alkaline or acid water per se but a composition as defined above which comprises it.

The expression "treatment or prevention" means that thanks to its properties, an electrolytic alkaline or acid water according to the invention or a composition which comprises it have been found to be effective for the treatment and remission of surface or deep skin or mucosa pathologies or lesions that are already occurring (for example healing of injuries or lesions of the skin or dermis, control and remission of bacterial, mycotic or viral infections affecting the skin or dermis or mucosa), or to reduce the risk of developing deep or superficial pathologies or lesions of the skin or mucosa.

It is also understood that the treatment effects and prevention also apply to disorders which are systemic but in which the etiogenesis can be ascribed to the cutaneous penetration of infectious agents. Early treatment of the skin infection in fact allows elimination of the infectious agent before it achieves systemic diffusion.

In a preferred embodiment, the invention provides a use for the waters of the present invention in the treatment or prevention of skin or dermis or mucosa disorders or lesions, preferably selected from: (i) physical injuries and lesions of the skin or mucosa, including abrasions, ulcers, burns, sunburns and bedsores, (ii) bacterial infections affecting the skin or dermis or mucosa including cellulites, folliculitis, boils, carbuncles, erysipelas, erythrasma, impetigo, paronychia, and staphylococcal infections, (iii) parasitic infections including lice, creeping eruption and scabies, (iv) viral infections affecting the skin or dermis or mucosa including cold sores (including herpes simplex virus Type 1 and Type 2), HIV, moluscum contagiosum, chicken pox, measles, shingles and warts, (v) fungal infections affecting the skin or dermis including candidiasis, athlete's foot (tinea pedis), jock itch (tinea cruris), ringworm (tinea corporis), face fungus (tinea faciei), tinea versicolor, fungal nail infections, and fungal hair infections, (vi) allergic, inflammatory and immunological reactions, such as irritations and erythemas, affecting the epidermis and/or dermis or mucosa, including nettle rashes, dermatitides, eczemas, psoriases, and dandruff, and (vii) other disorders such as seborrhea, whiteheads, blackheads, and acne.

The expression "surface or deep skin lesions or pathologies" references preferably:

cutaneous phenomena associated with allergic, inflammatory and immunological reactions, such as irritations and erythemas, affecting the epidermis and/or dermis. Examples of irritations are nettle rashes, dermatitides (allergic or contact-related), eczemas, psoriases and dandruff. For treatment of psoriasis, the effectiveness of the water according to the invention is probably due to the exfoliating effect of the active chlorine contained therein;

superficial or deep cutaneous phenomena caused by bacterial and/or mycotic and/or viral infections, and/or fungal infections, including athlete's foot or tinea pedis, and lesions or abrasions of the skin and/or dermis, such as ulcers (including diabetic ulcers), burns, sunburns and bedsores.

The broad-spectrum biocidal functions exhibited by the electrolytic acidic waters of the invention and by the compositions that comprise them are confirmed not only by the results of the tests on specific pathogens but also by the fact that the product according to the present invention is capable of degrading completely the nucleic acids of pathogens.

As mentioned, the acid water according to the invention can be used for the treatment and remission of burns or sunburns of the skin or for the healing of wounds, by virtue of their low toxicity and high penetration capacity. One aspect which demonstrates the high penetration capacity of the alkaline and acid waters described here is its high swelling power seen on tissues which are dehydrated and preserved in appropriate banks while waiting for transplants in humans or animals (reimplantation tissues).

Moreover, the aqueous solution according to the invention, in view of its broad range of action against microorganisms or viruses, can be used for example to eliminate parasitoses of viral and/or bacterial origin of plants intended for food use (for example fruits, leafy vegetables, et cetera) or for domestic/decorative use (apartment plants, flowers).

In another aspect, the present invention relates to the use of an electrolytic acid water as defined above or to a composition which comprises it to sanitize a substrate. Advantageously the substrate is selected among 1) inanimate objects and surfaces, 2) surfaces of the human or animal body, and 3) surfaces of isolated parts of a human or animal body.

Preferred inanimate surfaces and objects are domestic spaces and objects, medical and medical-surgical devices and instruments (for example teats, endoscopes or other medical tools), contact lenses and optical instruments in general, surfaces of edible products, for example fruits or vegetables.

Preferred surfaces of the human or animal body are parts of a patient or surgeon before or after surgery, and human breasts or animal udders. Preferred surfaces of isolated parts of the human or animal body are human or animal reimplantation tissues, such as tendons, wherein said tissues can be dehydrated or not.

In a further aspect, the present invention relates to the use of an electrolytic alkaline or acidic water as defined above or of a composition which comprises it for cosmetic treatment of the human or animal body or of isolated parts thereof.

Cosmetic use relates in particular to the treatment of the skin, particularly the skin of areas of the human body which are subject to rashes, such as the skin of hands, feet and face, that would benefit from an acid or alkaline treatment. In a preferred embodiment the water is used as a delivery vehicle for vitamin E, vitamin B1, vitamin B2, vitamin B6, vitamin B12, vitamin C, and other topically applied nutrients, to increase the absorption thereof.

Moreover, the alkaline and acid waters according to the invention have exhibited a surprising capacity to dissolve the cutaneous lipid secretion, so that they can be used in the cosmetic treatment of acne and blackheads.

Also in the cosmetic field, importance is given to the property exhibited by the alkaline and acid waters according to the invention to dissolve most of the chemical residues left by the application of cosmetics to the skin and already partially absorbed by the surface layers of said skin, and to the capacity to remove from the skin the fine powders which are generated by pollution and are adsorbed thereon.

In another aspect, the present invention relates to the use of an electrolytic alkaline or acid water as defined above or of a composition which comprises it to rehydrate human or animal dehydrated tissues for reimplantation.

Tissues for human or animal reimplantation are preserved, after being explanted from the donor and while waiting for reimplantation, in appropriately provided sterile banks, usually after dehydration (for example by freeze drying), so as to slow and prevent the growth of bacteria. When the alkaline or acidic water according to the invention has been used to rehydrate the tissues before reimplantation, a drastic reduction of rehydration times has been observed compared to the aqueous solutions conventionally used for this purpose. The application described above was unthinkable for conventional alkaline and acid waters due to their low purity (especially in terms of heavy metals) and low stability.

When the water is used per se without integration into a particular composition or dosage form, it may be used exactly as it is produced, or it may be altered by, for example, the addition of a pH modifying agent. The alkaline water may also be modified prior to integration into a finished formulation. For example, the pH of the alkaline water can be reduced by mixing it with an acid (i.e. an organic acid) or with acid water produced by electrolysis. A preferred acid with which to modify the alkaline water is lactic acid. In an exemplary embodiment, the pH of the water is adjusted so that the pH of the water is less than or equal to 8, and greater than or equal to 3. Preferred ranges include from 3 to 4, from 4 to 5, from 5 to 6, from 6 to 7, and from 7 to 8.

When integrated into a finished formulation, the final product can be defined by several physical parameters including viscosity and pH. The final pH of the topical composition may be adjusted for stability or physiologic reasons, and preferably ranges from about 3.0 to about 8.0, more preferably from about 3.5 to about 7.0, and most preferably from about 4.0 to about 5.0, or from about 5.0 to about 6.0.

When integrated into a topical formulation, the alkaline or acid water can be present in any percentage that does not compromise the structure of the desired composition. The formulation preferably comprises from about 20 to about 95 wt. % of the alkaline water, and more preferably comprises from about 50, 70 or 80 wt. % to about 90 wt. % water. The excipients used may be any excipients conventional in the topical pharmaceutical and cosmetic arts.

Topical Excipients

Preferred pharmaceutically acceptable excipients and carriers are excipients and carriers usually used to prepare topical disinfectant compositions or to prepare skin treatment compositions. Examples are polymers of vegetable origin (derivatives of cellulose or starch) or synthetic ones (acrylic polymers) or animal-derived polymers (collagen).

The expression "excipients and carriers used for disinfectant compositions" is used to reference ingredients which are commonly used to prepare:
  disinfectant compositions for edible products (food sector),
  disinfectant compositions for environments, devices and medical-surgical instruments,
  disinfectant compositions for human or animal reimplantation tissues,
  disinfectant compositions for cleaning and maintaining the hygiene of contact lenses and optical material in general,
  disinfectant compositions for home surfaces and environments.

In certain embodiments the topical formulation may include at least one water-insoluble, pharmacologically approved, alkyl cellulose or hydroxyalkyl cellulose, and the like. Alkyl cellulose or hydroxyalkyl cellulose polymers for use in this invention include ethyl cellulose, propyl cellulose, butyl cellulose, cellulose acetate, hydroxypropyl cellulose, hydroxybutyl cellulose, and ethylhydroxyethyl cellulose, alone or in combination. In addition, a plasticizer or a cross linking agent may be used to modify the polymer's characteristics. For example, esters such as dibutyl or diethyl phthalate, amides such as diethyldiphenyl urea, vegetable oils, fatty acids and alcohols such as acid oleic and myristyl may be used in combination with the cellulose derivative. In other embodiments the formulation may contain liposoluble ingredients like tea polyphenols, aloe or other botanic ingredients.

In certain embodiments, the topical formulation may further include hydrocarbons such as liquid paraffin, Vaseline®, solid paraffin, microcrystalline wax, etc.; higher aliphatic alcohols such as cetyl alcohol, hexadecyl, alcohol, stearyl alcohol, oleyl alcohol, etc.; esters of higher fatty acids with higher alcohols such as beeswax, etc.; esters of higher fatty acids with lower alcohols such as isopropyl myristate, isopropyl palmitate, etc.; vegetable oils, modified vegetable oils, hydrous lanolin and its derivative, squalene, squalane; higher fatty acids such as palmitic acid, stearic acid, etc. and the like.

In certain embodiments, the topical formulation may further include emulsifiers and dispersing agents which include, for example, anionic, cationic and nonionic surfactants. Nonionic surfactants are preferred because of their low levels of irritation to skin. Typical of nonionic surfactants are fatty acid monoglycerides such as glyceryl monostearate, etc.; sorbitan fatty acid esters such as sorbitan monolaurate, etc.; sucrose fatty acid esters; polyoxyethylene fatty acid esters such as polyoxyethylene stearate, etc.; and polyoxyethylene higher alcohol ethers such as polyoxyethylene cetyl ether, polyoxyethylene oleyl ether, etc.

In certain embodiments of the present invention, the topical formulation may include a gelling agent such as methylcellulose, ethylcellulose, hydroxyethylcellulose, hydroxypropyl-cellulose, hydroxypropylmethylcellulose, carboxymethylcellulose, carbomer, and the like.

From what has been described above it is evident that the invention achieves the intended aim and objects, and in particular the aim of providing an electrolytic acid aqueous solution having characteristics which are already known but a much higher stability than conventional products.

The invention is susceptible of numerous modifications and variations, all of which are within the scope of the inventive concept expressed in the appended claims. All the details may be replaced with other technically equivalent elements and the materials may be different according to requirements without abandoning the scope of the invention. Other characteristics and advantages of the present invention will become better apparent from the description of the following preferred embodiments, intended exclusively by way of non-limiting examples.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

Example 1

Preparation of Electrolytic Cell

Starting Materials:
Electrode: Titanium processed after passivation is used as the base carrier material for the electrode.
$TiO_2$, $Pt/ZrO_2$, $SnO_2$, $Ta_2O5$, and $IrO_2$ powders having a mean particle diameter of 40-80 nm are obtained by hydrothermal chemical processing.

Step 1. Formed a $TiO_2$ base carrier layer by plasma spraying, sinter the carrier layer for 30 minutes at a temperature of temperature 550° C., and anneal the sintered layer for 60 minutes.

Step 2. Coat the carrier layer from step 1 with a solution formed by dissolving $SnO_2$ in hydrochloric acid, and ultrasonically vibrating the solution for 20 minutes. The solution is then coated on the carrier layer, sintered for 30 minutes at 400° C., and annealed for 50 minutes.

Step 3. Coat the carrier material from step 2 with a solution formed by dissolving $IrO_2$ in hydrochloric acid, and vibrating ultrasonically for 20 minutes. The applied coating is then sintered for 30 minutes at a temperature of 400° C., and annealed for 50 minutes.

Step 4. Coat the carrier material from step 3 with a solution formed by dissolving $IrO_2$ in hydrochloric acid and ultrasonically vibrating for 20 minutes. The applied coating is then sintered for 40 minutes at a temperature of 450° C., and annealed for 55 minutes.

Step 5. Coat the carrier material from step 4 with a solution formed by dissolving $Ta_2O5$ in hydrochloric acid and ultrasonically vibrating for 20 minutes. The coated layer is then sintered for 30 minutes at 450° C., and annealed for 60 minutes.

Step 6. Coat the carrier material from step 5 with a solution formed by dissolving $Ta_2O5$ in hydrochloric acid and vibrating for 20 minutes with an ultrasonic device. The coated layer is then sintered for 40 minutes at 450° C., and annealed for 60 minutes.

Step 7. Coat the carrier material from step 6 with a solution formed by dissolving $Ta_2O5$ in a 1:1:1 mixture of hydrochloric acid, normal butanol and isopropanol, and ultrasonically vibrating for 30 minutes. The coated layer is then sintered for 40 minutes at 450° C., and annealed for 60 minutes.

Step 8. Coat the carrier material from step 7 with a solution formed by dissolving $Pt/ZrO_2$, in a 1:1:1 mixture of hydrochloric acid, normal butanol and isopropanol (ratio 1:1:1), and ultrasonically vibrating the solution for 30 minutes. The coated layer is then sintered for 40 minutes at 450° C., and annealed for 60 minutes.

Step 9. Coat the carrier material from step 8 with a solution formed by dissolving $Pt/ZrO_2$ in a 1:1:1 mixture of hydrochloric acid, normal butanol and isopropanol, and ultrasonically vibrating the mixture for 30 minutes. The coated layer is then sintered for 40 minutes at 450° C., and annealed for 60 minutes.

Separation Membrane:
Step 1. Nano-ceramic powders of $ZrO_2$ and $Al_2O_3$ are first obtained by hydrothermal chemical processing. The powders obtained are defined by the following features:

Particle diameter: 50-60 nm. (80-85%)

Weight percentage 70%: 30% (particles inside range vs. particles outside range)

Step 2. The mixture of two nano-composite powders is fed into a cubic metal container, and pressed under a hydraulic press to form a billet for sintering with a thickness of 10-12 mm.

Step 3. The billet is sintered by packing into a ceramic container in a furnace at a temperature of 1050-1150° C. The temperature is increased at a rate at 3.5-4° C./minute, for about 2 hours, forming a final ceramic separation membrane with a thickness of 2.5-3 mm.

Example 2

Characterization of Alkaline Water

Using the process and electrolytic cell described in Example 1, alkaline water meeting the following chemical characteristics can be produced:
pH: 8.5-12.5 (preferably 10-12)
ORP: −200 to −900 mV (preferably −600 to −900 mV)
Half line width of $^{17}$O (oxygen isotope 17) NMR test: 45-51 Hz.
No heavy metals detected (i.e. free of heavy metals)
In examples 3-5, the alkaline water used had a pH of 12.0 and an ORP of −750 mV, except for test 3 of example 4, in which water having a pH of 9.0, and an ORP of −250 mV was used.

Example 3

In Vitro Testing Using Alkaline Water of Example 2

Test 1.
Based on LD50 (medium lethal dose) testing in mice, the alkaline water of Example 2 is categorized as having no toxicity.
Test 2.
No irritation is detected in dermal irritation testing.
Test 3.
No ophthalmic irritation is detected.
Test 4.
No irritation of the vaginal mucosa is detecting.
Test 5.
Based on accumulation toxicity testing and an accumulative coefficient K>5, the accumulative toxicity of the alkaline water of example 2 is categorized as weak.
Test 6.
The alkaline water of example 2 was determined not to cause any morphological changes to the micronucleus of a polychromatic erythrocyte.

Example 4

Anti-Microorganism Study

The average inhibitory rate of the alkaline water (ph=13.0) of example 2 on *E. coli* in culture after 3 minutes of processing time was determined to be 70%.

Example 5

Topical Alkaline Formulations

Using alkaline electrolyzed water that meets the specifications described in Table A, topical formulations described in Tables B-F were prepared. Viscosity measurements were made using a Brookfield DVII+Pro spindle 6 at 10 rpm and 20° C.

TABLE A

ALKALINE WATER SPECIFICATIONS

| DETERMINATION | SPECIFICATIONS |
|---|---|
| Appearance | Colourless liquid |
| Odour | Odourless |
| pH | 9.0-12.5 |
| ORP mV (at release) | −900/−200 |
| ORP mV (after contact with air) | About 300 |
| $^{17}$O-NMR (Hz) | <50 |

TABLE B

LIST OF FORMULATIONS TESTED

| NAME | BATCH |
|---|---|
| ALKALINE NANOCLUSTERED WATER pH 11 | LCOX/11 |
| CREAM prepared with DEIONISED NORMAL WATER ALKALINISED by NaOH till pH 11 and ACIDIFIED with LACTIC ACID till pH around 7 | LCOX/44 PLACEBO OF LCOX/43 |
| CREAM prepared with ALKALINE NANOCLUSTERED WATER ACIDIFIED by LACTIC ACID till pH around 7 | LCOX/43 |
| CREAM prepared with DEIONISED NORMAL WATER ALKALINISED by NaOH till pH 11 and ACIDIFIED with LACTIC ACID till pH around 4 | LCOX/30 PLACEBO OF LCOX/29 |
| CREAM prepared with ALKALINE NANOCLUSTERED WATER ACIDIFIED by LACTIC ACID till pH around 4 | LCOX/29 |

TABLE C

LCOX/44 FORMULATION

| Raw material Trade Name | INCI Name | Manufacturer | % |
|---|---|---|---|
| DEIONISED NORMAL WATER ALKALINISED by NaOH till pH 11 and ACIDIFIED with LACTIC ACID till pH around 7 | AQUA SODIUM HYDROXIDE LACTIC ACID | APR | 81 |
| FDA 15 Pharma 19 | PARAFFINUM LIQUIDUM | Brenntag | 6.5 |
| Nikkomulese 41 | POLYGLYCERYL-10 PENTASTEARATE BEHENYL ALCOHOL SODIUM STEAROYL LACTYLATE | Nikkol Chemical | 5 |
| Sepigel 305 | POLYACRYLAMIDE, C13-14 ISOPARAFFIN, LAURETH-7 | Seppic | 2.5 |
| Symdiol 68 | 1,2 HEXANEDIOL CAPRYLYL GLYCOL | Symrise | 1.25 |
| MP Diol Glycol | METHYLPROPANEDIOL | Lyondell | 3.75 |

Appearance: Viscous Cream
Color: White
Odour: Characteristic
pH at 20° C.: 5.18
viscosity: (57.000 mPas)

TABLE D

LCOX/43 FORMULATION

| Raw material Trade Name | INCI Name | Manufacturer | % |
|---|---|---|---|
| ALKALINE NANOCLUSTERED WATER ACIDIFIED by LACTIC ACID till pH around 7 | For ALKALINE NANOCLUSTERED WATER: to be assigned LACTIC ACID | Akuatech | 81 |
| FDA 15 Pharma 19 | PARAFFINUM LIQUIDUM | Brenntag | 6.5 |
| Nikkomulese 41 | POLYGLYCERYL-10 PENTASTEARATE BEHENYL ALCOHOL SODIUM STEAROYL LACTYLATE | Nikkol Chemical | 5 |
| Sepigel 305 | POLYACRYLAMIDE, C13-14 ISOPARAFFIN, LAURETH-7 | Seppic | 2.5 |
| Symdiol 68 | 1,2 HEXANEDIOL CAPRYLYL GLYCOL | Symrise | 1.25 |
| MP Diol Glycol | METHYLPROPANEDIOL | Lyondell | 3.75 |

Appearance: Viscous Cream
Color: White
Odour: Characteristic
pH at 20° C.: 5.05
viscosity: (55.000 mPas)

TABLE E

LCOX/30 - FORMULATION

| Raw material Trade Name | INCI Name | Manufacturer | % |
|---|---|---|---|
| DEIONISED NORMAL WATER ALKALINISED by NaOH till pH 11 and ACIDIFIED with LACTIC ACID till pH around 4 | AQUA SODIUM HYDROXIDE LACTIC ACID | APR | 81 |
| FDA 15 Pharma 19 | PARAFFINUM LIQUIDUM | Brenntag | 6.5 |
| Nikkomulese 41 | POLYGLYCERYL-10 PENTASTEARATE BEHENYL ALCOHOL SODIUM STEAROYL LACTYLATE | Nikkol Chemical | 5 |
| Sepigel 305 | POLYACRYLAMIDE, C13-14 ISOPARAFFIN, LAURETH-7 | Seppic | 2.5 |
| Symdiol 68 | 1,2 HEXANEDIOL CAPRYLYL GLYCOL | Symrise | 1.25 |
| MP Diol Glycol | METHYLPROPANEDIOL | Lyondell | 3.75 |

Appearance: Viscous Cream
Color: White
Odour: Characteristic
pH at 20° C.: 4.41
viscosity: (60.000 mPas)

TABLE F

LCOX/29 - FORMULATION

| Raw material Trade Name | INCI Name | Manufacturer | % |
|---|---|---|---|
| ALKALINE NANOCLUSTERED WATER ACIDIFIED by LACTIC ACID till pH around 4 | For ALKALINE NANOCLUSTERED WATER: to be assigned LACTIC ACID | Akuatech | 81 |
| Paraffimum Liquidum FDA 15 Pharma 19 | PARAFFINUM LIQUIDUM | Brenntag | 6.5 |
| Nikkomulese 41 | POLYGLYCERYL-10 PENTASTEARATE BEHENYL ALCOHOL SODIUM STEAROYL LACTYLATE | Nikkol Chemical | 5 |
| Sepigel 305 | POLYACRYLAMIDE, C13-14 ISOPARAFFIN, LAURETH-7 | Seppic | 2.5 |
| Symdiol 68 | 1,2 HEXANEDIOL CAPRYLYL GLYCOL | Symrise | 1.25 |
| MP Diol Glycol | METHYLPROPANEDIOL | Lyondell | 3.75 |

Appearance: Viscous Cream
Color: White
Odour: Characteristic
pH at 20° C.: 4.43
viscosity: (57.000 mPas)

Example 6

TEER Testing of Topical Alkaline Formulations

The formulations described in Tables B-F were tested for their effect on trans-epithelial electrical resistance according to the following procedure. Results are reported in FIGS. 2-6.

Procedure 1 ml of saline solution is directly applied on the tissue placed in a 6 well plate containing 4 ml of saline solution as well.

The instrument Millicell-ERS (range 0-20 kΩ) is placed with the two electrodes in the two chambers and the measure is recorded directly and reported in the laboratory note book.

Five measurements for each tissue have been done: because of the variability within the tissues the measurement done at t=0 has been taken as basal value and reference of each single tissue.

Day 1: Reception of the Reconstructed Human Epidermids (RHEs) and Basal Tier Measurements At the arrival the tissues have been placed in 6 well plates with maintenance medium (SkinEthic) for 2 hours before the TEER measurements.

The basal TEER value is measured on all the tissue as described in the method.

The tissues have been recovered in maintenance medium (1 ml) and the test items have been applied at the dose of 50 μl.

Tissues have been finally incubated at 37° C. in 5% $CO_2$ incubator.

Day 2: 24 h Exposure Measurements

The tissues have been rinsed with saline solution and the second TEER measurement, corresponding to the 24 h exposure, has been performed.

The RHEs have been recovered in fresh maintenance medium (1 ml) for a 24 h post-incubation time.

Day 3: 24 h+24 h Post Incubation Measurements

Figure 2:
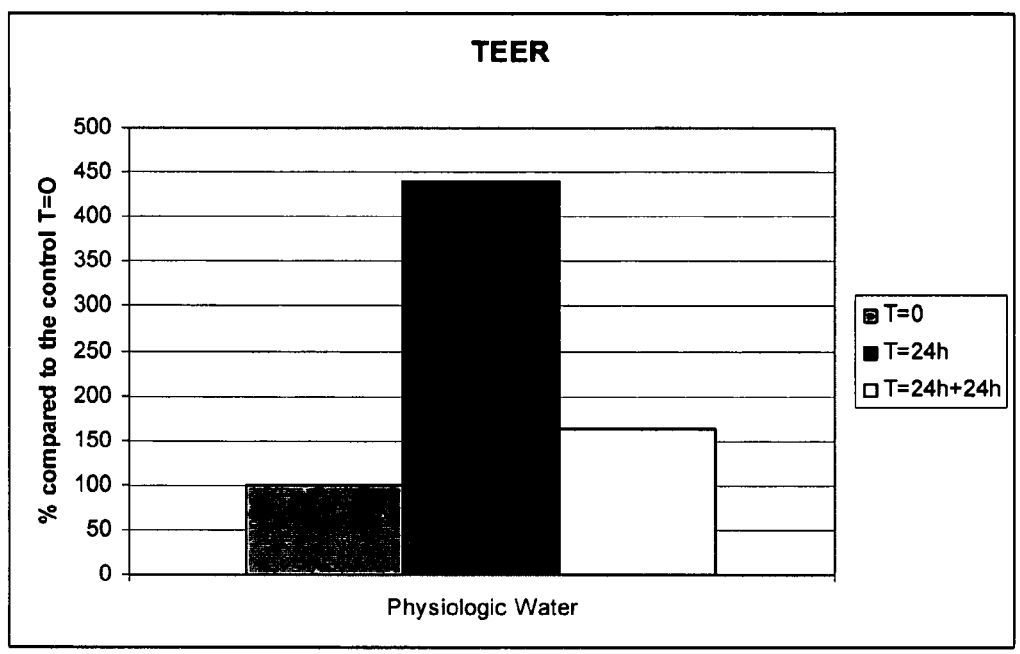
FIG. 2 is a bar graph depicting the results of trans-epithelial electrical resistance testing of a tissue sample in physiologic water as described in Example 7.

The last TEER measurement is performed with the same methods; the samples have been processed as described in 4.2. for further analysis Results As shown in FIG. 2, the saline solution (physiologic water) used as reference has induced a regular increase of TEER and the behaviour is confirmed by both exposures:

The 24 h results first means that the permeability of the tissue has not been modified by the treatment and secondly that the tissue thickness is increased as expected.

The results at 24 h with the successive rinsing and post incubation of 24 h show that the TEER, even if reduced in absolute value, is still over the basal level (T=0 h) and consequently this treatment globally has not modified the permeability of the tissue.

Figure 3:
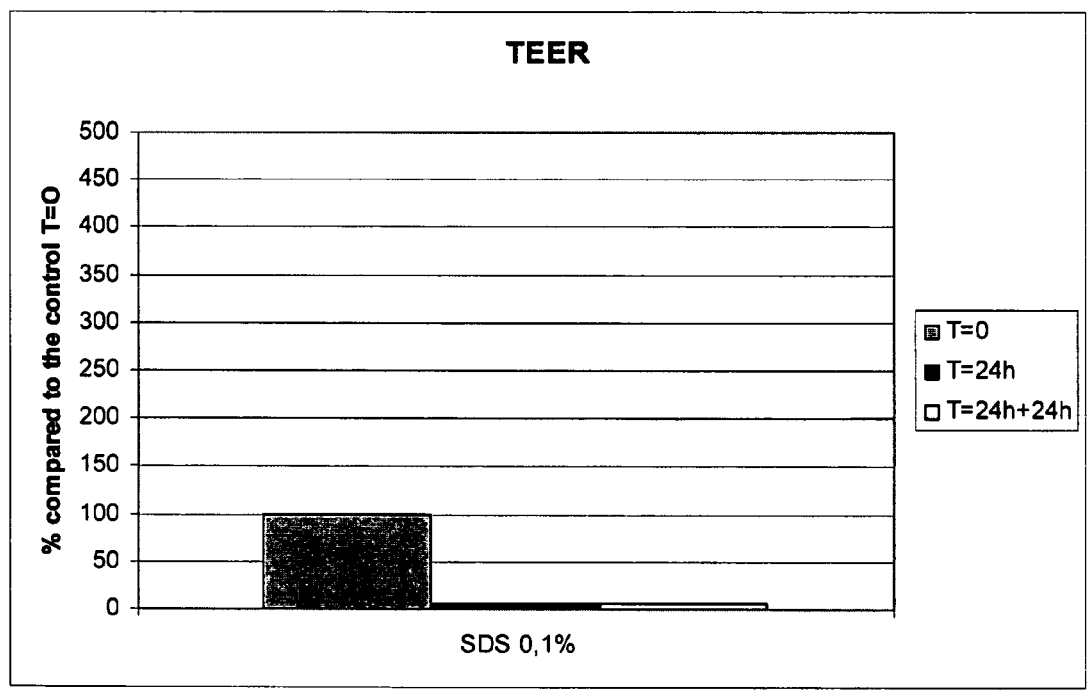
FIG. 3 is a bar graph depicting the results of trans-epithelial electrical resistance testing of a tissue sample in SDS as described in Example 7.

As shown in FIG. 3, The sodium dodecyl sulphate (SDS 0.1%), solution has induces a strong decrease of TEER and this behaviour is due to its irritating and toxic effect that, breaking the tissue, provoke a damage in the barrier function.

Figure 4:
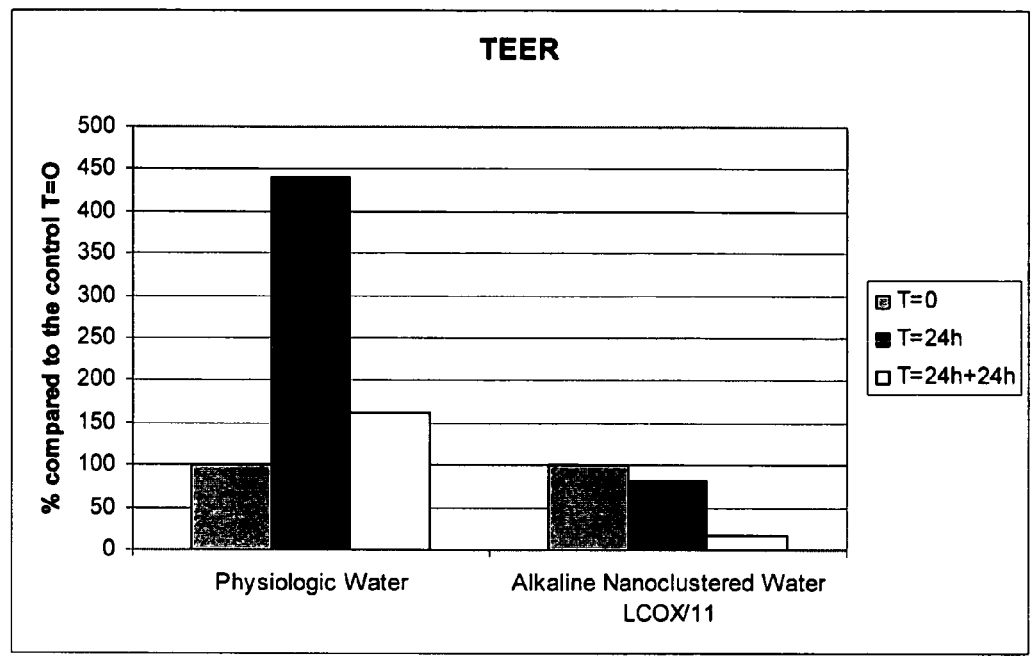
FIG. 4 is a comparison bar graph depicting the results of trans-epithelial electrical resistance testing of a tissue sample in physiologic water and a tissue sample in reduced NMR half line width alkaline water, as described in Example 7.
Figure 5:
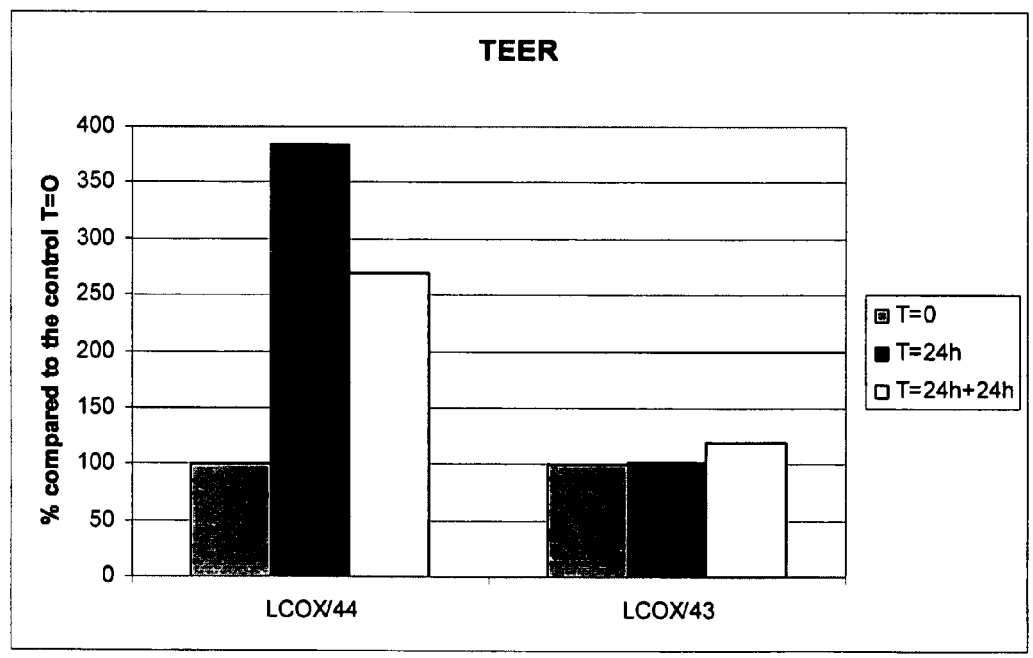
FIG. 5 is a comparison bar graph depicting the results of trans-epithelial electrical resistance testing of a tissue sample in a placebo cream and a tissue sample in a cream made from reduced NMR half line width alkaline water, as described in Example 7.
Figure 6:
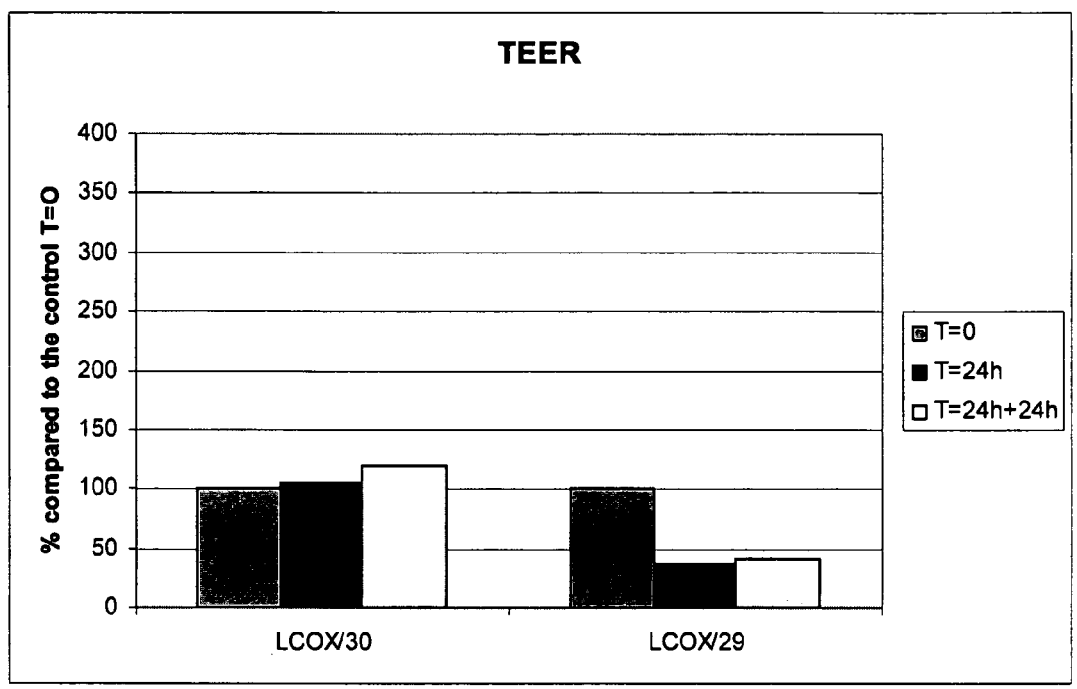
FIG. 6 is a comparison bar graph depicting the results of trans-epithelial electrical resistance testing of a tissue sample in a placebo cream and a tissue sample in a cream made from reduced NMR half line width alkaline water, as described in Example 7.

As shown in FIGS. 4-6, a TEER decrease is observed in all the Nano-clustered waters and related formulations, compared to related placebo. We can be quite confident that the Nano-clustered waters and related formulations decrease the TEER because they are able to increase the tissues permeability and the paracellular flux of water and ions, without provoking toxic effects.

Example 7

Hydrating Power of Alkaline Water on Dehydrated Organic Tissues (Tendons)

A dehydrated section of tendon is dipped into the gels described in Tables G and H, and left for 60 minutes and pull out and observed.

TABLE G

Gel with Alkaline Water of Present Invention

| Raw material Trade Name | INCI Name | Manufacturer | % |
| --- | --- | --- | --- |
| ALKALINE NANOCLUSTERED WATER | To be assigned | Akuatech | 88.85 |
| MP Diol Glycol | METHYLPROPANEDIOL | Lyondell | 3.75 |
| Propylene Glycol USP | PROPYLENE GLYCOL | Brenntag | 2.00 |
| Glycerin | GLYCERIN | Sabo | 2.00 |
| Natrosol 250 MR | HYDROXYETHYLCELLULOSE | Hercules | 1.50 |
| Symdiol 68 | 1,2 HEXANEDIOL CAPRYLYL GLYCOL | Symrise | 1.25 |
| Cremophor RH 40 | PEG-40 HYDROGENATED CASTOR OIL | Basf | 0.40 |
| Lactic Acid | LACTIC ACID | Brenntag | 0.15 |
| Disodium EDTA | Disodium EDTA | Basf | 0.10 |

Appearance: Viscous Cream
Color: White
Odour: Characteristic
pH at 20° C.: 6.36
Viscosity: (17.500 mPas)

TABLE H

Placebo Gel with Deionised Normal Water Alkalinised by NaOH till pH 11

| Raw material Trade Name | INCI Name | Manufacturer | % |
| --- | --- | --- | --- |
| DEIONISED NORMAL WATER ALKALINISED by NaOH till pH 11 | AQUA | APR | 88.85 |
| MP Diol Glycol | METHYLPROPANEDIOL | Lyondell | 3.75 |
| Propylene Glycol USP | PROPYLENE GLYCOL | Brenntag | 2.00 |
| Glycerin | GLYCERIN | Sabo | 2.00 |
| Natrosol 250 MR | HYDROXYETHYLCELLULOSE | Hercules | 1.50 |

TABLE H-continued

Placebo Gel with Deionised Normal Water Alkalinised by NaOH till pH 11

| Raw material Trade Name | INCI Name | Manufacturer | % |
|---|---|---|---|
| Symdiol 68 | 1,2 HEXANEDIOL CAPRYLYL GLYCOL | Symrise | 1.25 |
| Cremophor RH 40 | PEG-40 HYDROGENATED CASTOR OIL | Basf | 0.40 |
| Lactic Acid | LACTIC ACID | Brenntag | 0.15 |
| Disodium EDTA | Disodium EDTA | Basf | 0.10 |

Appearance: Viscous Cream
Color: White
Odour: Characteristic
pH at 20° C.: 6.28
Viscosity: (18.000 mPas)

The alkaline gel of the present invention resulted in a 25.62% increase in tendon volume. The placebo gel resulted in a 14.58% increase in tendon volume.

Example 8

Additional Alkaline Formulations

Tables I-O present examples of other topical formulations for use in the present invention.

TABLE I

Cream Example

| RAW MATERIAL TRADE NAME | INCI NAME | % |
|---|---|---|
| ALKALINE NANOCLUSTERED WATER + LACTIC ACID | TO BE ASSIGNED LACTIC ACID | TO 100 |
| FDA 15 PHARMA 19 | PARAFFINUM LIQUIDUM | 6.5 |
| NIKKOMULESE 41 | POLYGLYCERYL-10 PENTASTEARATE BEHENYL ALCOHOL SODIUM STEAROYL LACTYLATE | 5.0 |
| MP DIOL GLYCOL | METHYLPROPANEDIOL | 3.75 |
| SEPIGEL 305 | POLYACRYLAMIDE, C13-14 ISOPARAFFIN, LAURETH-7 | 2.5 |
| SYMDIOL 68 | 1,2 HEXANEDIOL CAPRYLYL GLYCOL | 1.25 |

TABLE J

Cream Example

| RAW MATERIAL TRADE NAME | INCI NAME | % |
|---|---|---|
| ALKALINE NANOCLUSTERED WATER + LACTIC ACID | TO BE ASSIGNED LACTIC ACID | TO 100 |
| PROPYLENE GLYCOL USP | PROPYLENE GLYCOL | 10.0 |
| DERMOL 88/DRAGOXAT EH | ETHYLHEXYL ETHYL HEXANOATE | 6.0 |
| NIKKOMULESE 41 | POLYGLYCERYL-10 PENTASTEARATE BEHENYL ALCOHOL SODIUM STEAROYL LACTYLATE | 5.0 |
| SEPIGEL 305 | POLYACRYLAMIDE, C13-14 ISOPARAFFIN, LAURETH-7 | 4.0 |
| MP DIOL GLYCOL | METHYLPROPANEDIOL | 3.75 |
| JOJOBA OIL | *BUXUS CHINENSIS* | 2.0 |
| SEPICIDE C 8 G | CAPRYLOYL GLYCINE | 1.00 |
| SHEA BUTTER | BUTYROSPERUM PARKII BUTTER | 1.00 |
| DISODIUM EDTA | DISODIUM EDTA | 0.1 |

TABLE K

Cream Example

| RAW MATERIAL TRADE NAME | INCI NAME | % |
|---|---|---|
| ALKALINE NANOCLUSTERED WATER + LACTIC ACID | TO BE ASSIGNED LACTIC ACID | TO 100 |
| POLAWAX GP 200 | CETEARYL ALCOHOL PEG-20 STEARATE | 10.0000 |
| BURRO DI KARITE' RAFFINATO | BUTYROSPERMUM PARKII BUTTER | 2.5000 |
| SABONAL C 1618 30/70 | CETEARYL ALCOHOL | 2.5000 |
| BASHYAL | AQUA, SODIUM HYALURONATE | 2.0000 |
| GLICERINA | GLYCERIN | 2.0000 |
| LINCOL BAS | C 12-15 ALKYL BENZOATE | 2.0000 |
| UVINUL MC80 | ETHYL HEXYL METHOXYCINNAMATE | 2.0000 |
| SOPSIL 350 G | DIMETHICONE | 1.2000 |
| LINCOL 40 | ETHYL HEXYL PALMITATE | 1.0000 |
| MIRASIL CM 5 | CYCLOPENTASILOXANE | 1.0000 |
| OLIO DI MANDORLE DOLCI | *PRUNUS AMYGDALUS DULCIS* OIL | 1.0000 |
| FENOSSIETANOLO | PHENOXYETHANOL | 0.7000 |
| PREVAN | SODIUM DEHYDROACETATE | 0.3000 |
| CRISTAL 326139 | PARFUM | 0.1500 |
| NIPAGIN M | METHYLPARABEN | 0.1500 |
| NIPASOL M | PROPYLPARABEN | 0.1500 |
| ALLANTOINA POLVERE | ALLANTOIN | 0.1000 |
| EDTA BISODICO | DISODIUM EDTA | 0.1000 |
| NATURAL EXTRACT AP | BETAINE | 0.1000 |
| VITAMINA E ACETATE | TOCOPHERYL ACETATE | 0.0500 |
| ARISTOFLEX AVC | AMMONIUM ACRYLOYLDIMETHYLTAURATE/ VP COPOLYMER | 0.0350 |
| ALOE VERA GEL FREEZE DRIED POWDER 200:1 | *ALOE BARBADENSIS* GEL | 0.0010 |

TABLE L

Cream Example

| RAW MATERIAL TRADE NAME | INCI NAME | % |
|---|---|---|
| ALKALINE NANOCLUSTERED WATER + LACTIC ACID | TO BE ASSIGNED LACTIC ACID | TO 100 |
| ACIFRUCTOL P 63 | PROPYLENE GLYCOL, LACTIC ACID, AQUA, *SOLANUM LYCOPERSICUM* EXTRACT, *CITRUS MEDICA LIMONUM* EXTRACT, *CITRUS GRANDIS* EXTRACT, *VACCINIUM MYRTILLUS* EXTRACT, CITRIC ACID, MALIC ACID | 10.00 |
| SABONAL C 1618 30/70 | CETEARYL ALCOHOL | 5.50 |
| CRODAMOL OP LINCOL 40 | ETHYL HEXYL PALMITATE | 5.00 |
| DERMOIL HDE | ISOHEXADECANE, PPG-15 STEARYL ETHER | 4.00 |
| BRIJ 72 | STEARETH-2 | 3.00 |
| BRIJ 721 | STEARETH-21 | 2.50 |
| GLICERINA | GLYCERIN | 1.50 |
| SOPSIL 350 G DC 200/350 | DIMETHICONE | 1.00 |
| SODIO IDROSSIDO pellets | SODIUM HYDROXIDE | 1.00 |
| ISOCIDE PF | PHENOXYETHANOL, PROPYLENE GLYCOL, METHYLPARABEN, ETHYLPARABEN, PROPYLPARABEN | 0.80 |
| ALLANTOINA | ALLANTOIN | 0.50 |
| UNICIDE U 13 | IMIDAZOLIDINYL UREA | 0.30 |
| HIBISCUS 326091 | PARFUM | 0.15 |
| EDETA BD | DISODIUM EDTA | 0.10 |
| ACIDO 18 β GLICIRRETICO | GLYCYRRHETINIC ACID | 0.05 |

TABLE M

Gel Example

| RAW MATERIAL TRADE NAME | INCI NAME | % |
|---|---|---|
| ALKALINE NANOCLUSTERED WATER + LACTIC ACID | TO BE ASSIGNED LACTIC ACID | TO 100 |
| GLICOLE PROPILENICO | PROPYLENE GLYCOL | 15.00 |

TABLE M-continued

Gel Example

| RAW MATERIAL TRADE NAME | INCI NAME | % |
|---|---|---|
| SOLUBILISANT LRI | PEG-40 HYDROGENATED CASTOR OIL PPG-26 BUTETH-26, AQUA | 1.00 |
| CARBOPOL ULTREZ 10 | CARBOMER | 0.40 |
| CFF 15441 ACQUA MARINA | PARFUM, BHT | 0.35 |
| UNICIDE U 13 | IMIDAZOLIDINYL UREA | 0.30 |
| SODIO IDROSSIDO | SODIUM HYDROXIDE | 0.20 |
| EDTA BISODICO | DISODIUM EDTA | 0.10 |
| NIPAGUARD DMDMH | DMDM HYDANTOIN, AQUA | 0.10 |
| PLANTACTIVE PGL | DIPOTASSIUM GLYCYRRHIZATE | 0.05 |
| CM GLUCAN | SODIUM CARBOXYMETHYLBETAGLUCAN, IMIDAZOLIDINYL UREA, PHENOXYETHANOL, AQUA | 0.05 |

TABLE N

Gel Example

| RAW MATERIAL TRADE NAME | INCI NAME | % |
|---|---|---|
| ALCOOL ETILICO DS per COSMESI TIPO C | ALCOHOL DENAT | 40.00 |
| ALKALINE NANOCLUSTERED WATER + LACTIC ACID | TO BE ASSIGNED LACTIC ACID | TO 100 |
| GLICERINA | GLYCERIN | 5.00 |
| SOLUBILISANT LRI | PEG-40 HYDROGENATED CASTOR OIL PPG-26 BUTETH-26, AQUA | 0.80 |
| CARBOPOL ETD 2020 | ACRYLATE/C10-30 ALKYL ACRYLATE CROSSPOLYMER | 0.40 |
| AMP CG | AMINOMETHYLPROPANOL | 0.30 |
| CFF 15441 ACQUA MARINA | PARFUM, BHT | 0.30 |
| PLANTACTIVE PGL | DIPOTASSIUM GLYCYRRHIZATE | 0.30 |
| CM GLUCAN | SODIUM CARBOXYMETHYLBETAGLUCAN, IMIDAZOLIDINYL UREA, PHENOXYETHANOL, AQUA | 0.30 |
| EDTA BISODICO | DISODIUM EDTA | 0.10 |

TABLE O

Detergent Example

| RAW MATERIAL TRADE NAME | INCI NAME | % |
|---|---|---|
| ALKALINE NANOCLUSTERED WATER + LACTIC ACID | TO BE ASSIGNED LACTIC ACID | To 100 |
| ESAPON MG | AQUA MAGNESIUM LAURETH SULFATE, DISODIUM LAURETH SULFOSUCCINATE | 25.00 |
| ANFOPON B 4 AMPHOTENSID B 4 | AQUA, COCAMIDOPROPYL BETAINE, SODIUM CHLORIDE | 8.00 |
| ABIETOIL POLIPEPTIDE di SOIA | AQUA, POTASSIUM ABIETOYL HYDROLYSED SOY PROTEIN, PHENOXYETHANOL, METHYLPARABEN, ETHYLPARABEN, PROPYLPARABEN, BUTYLPARABEN | 2.50 |
| CFF 15441 ACQUA MARINA | PARFUM, BHT | 0.50 |
| UNICIDE U 13 | IMIDAZOLIDINYL UREA | 0.40 |
| NIPAGUARD DMDMH | DMDM HYDANTOIN, AQUA | 0.15 |
| EDTA BISODICO | DISODIUM EDTA | 0.10 |
| PLANTACTIVE PGL | DIPOTASSIUM GLYCYRRHIZATE | 0.10 |
| CM GLUCAN | SODIUM CARBOXYMETHYLBETAGLUCAN, IMIDAZOLIDINYL UREA, PHENOXYETHANOL, AQUA | 0.10 |
| ACIDO CITRICO | CITRIC ACID | 0.05 |

Example 9

Figure 7:
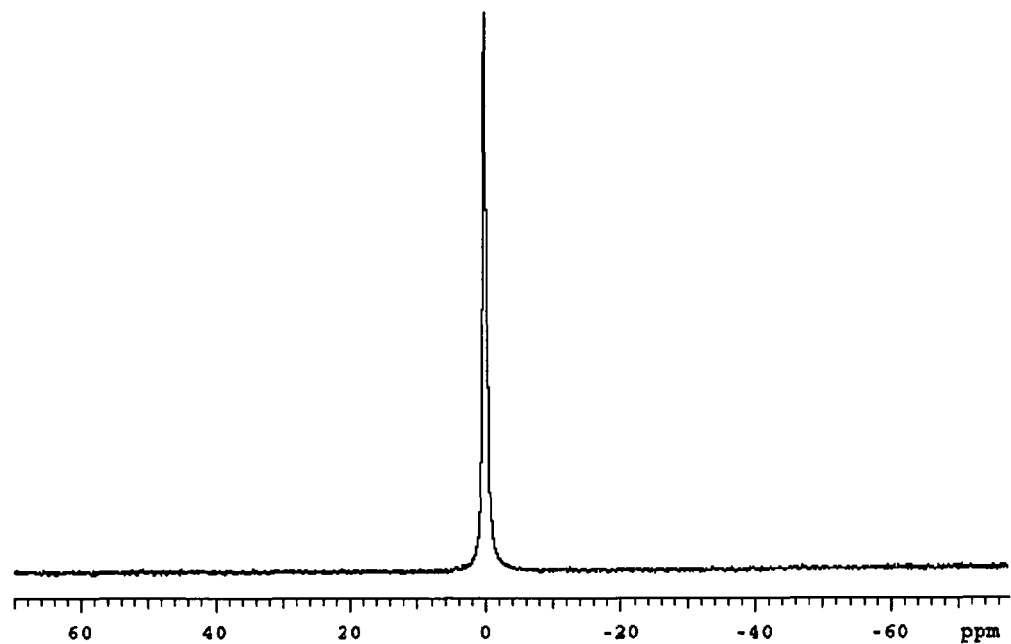
FIGS. 7 and 8 depict $^{17}O$ NMR spectroscopy data obtained on alkaline water produced by the methods of the present invention, for samples LCOIV/143 (after one month standing at 25° C., in a dark airtight glass bottle), and LCOIV/143 (after one month standing at 40° C., in a dark airtight glass bottle).
Figure 8:
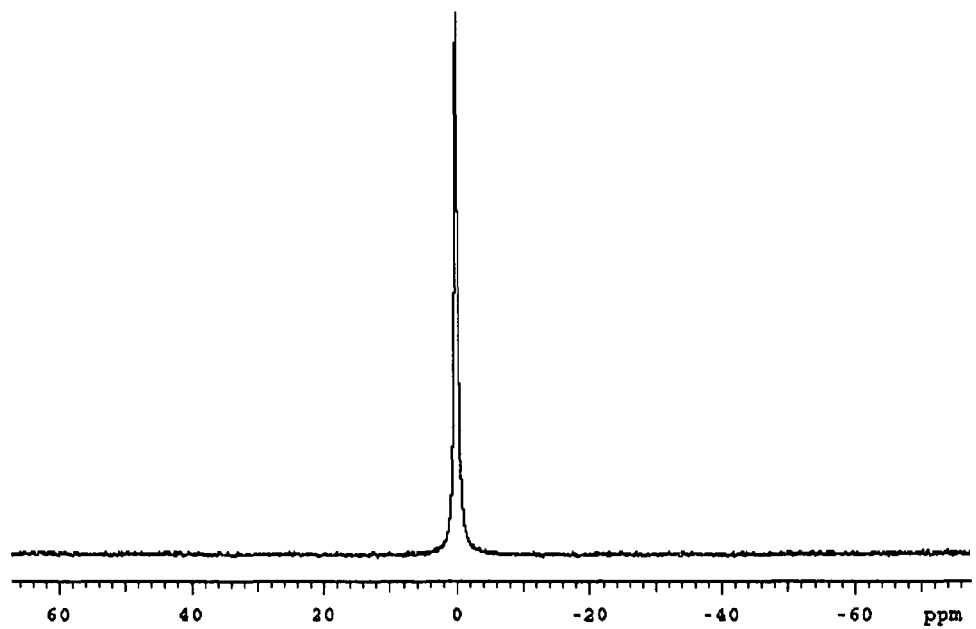

NMR Testing of Alkaline Water $^{17}$O NMR spectroscopy data was obtained on alkaline water produced by the methods of the present invention, and is reproduced in FIGS. 7 and 8, for samples LCOIV/143 (after one month standing at 25° C., in a dark airtight glass bottle), and LCOIV/143 (after one month standing at 40° C., in a dark airtight glass bottle). Half line width was recorded as 46.21 Hz and 46.10 for the LCOIV/143 samples reported in FIGS. 7 and 8, respectively. Data acquisition parameters are reported in Table P:

TABLE P

ACQUISITION PARAMETERS

Pulse Sequence: s2pul
Solvent: D20
Temp. 25.0 C./298.1 K
Acq. time 0.100 sec
Width 16260.2 Hz
OBSERVE 017, 81.3032545 MHz
DATA PROCESSING Sq. sine bell 0.100 sec
Shifted by −0.100 sec
FT size 16384

Example 10

Acid Water Specifications

TABLE Q

| DETERMINATION | SPECIFICATIONS |
|---|---|
| Appearance | Colourless liquid |
| Odour | Characteristic |

TABLE Q-continued

| DETERMINATION | SPECIFICATIONS |
|---|---|
| pH | <3.00 |
| ORP (mV) | >1100.0 |
| Free Chlorine Assay (mg/l) Spectrophotometric method | 40.0-70.0 |
| Total Chlorine Assay (mg/l) Spectrophotometric method | 40.0-70.0 |
| Total Chlorine Assay (mg/l) Iodometric method | 40.0-70.0 |
| Chloride Assay (mg/l) Mercurimetric method | <500.0 |
| $^{17}$O-NMR (MHz) | <50 |
| Heavy metals (ppm) | <10 ppm |
| Yttrium | <0.1 ppm |
| Zinc | <0.1 ppm |
| Iridium | <0.1 ppm |
| Titanium | <0.1 ppm |
| Zirconium | <0.1 ppm |
| Ruthenium | <0.1 ppm |

Example 11

Comparison of Physical Characteristics of Acid Water and Dermacyn®

TABLE R

| | ACIDIC NANOCLUSTERD WATER LOT LCOVI/57 | ACIDIC NANOCLUSTERD WATER LOT LCOX/5 | ACIDIC NANOCLUSTERD WATER LOT LCOX/1 | DERMACYN® WOUND CARE * LOT H070822-01-NL |
|---|---|---|---|---|
| Appearance | colourless liquid with light chlorine smell (like swimming pool) | Same | Same | Same |
| Free Chlorine Assay (mg/l) Spectrophotometric Method | 53.1 | 48.6 | 49.9 | 55.0 |
| Total Chlorine Assay [mg/l] Spectrophotometric Method | 52.1 | 48.6 | 49.0 | 54.9 |
| Total Chlorine Assay (mg/l) Iodometric Method | 60.6 | 54.9 | 56.7 | 64.7 |
| Chloride Assay (mg/l) UNI 24012 (Mercurimetric method) | 138 | 194.0 | 183.4 | 109.3 |
| Chlorites µg/l (as $ClO_2$) by EPA 300.1 1997 (detection limit 100 µg/l) | <100 | 100 | <100 | <100 |
| Chlorates mg/l by EPA 300.1 1997 (detection limit 0.1 mg/l) | 1.20 | 1.5 | 0.9 | 26 |
| pH (as is by Mettler Toledo pH meter Met Rohm 744) | 2.59 | 2.71 | 2.81 | 6.96 (range from manufacturer information 6.2-7.8) |
| ORP by Mettler Toledo PT4805-60-88TE-S7/120 combination redo electrode | 1151.8 | 1121.7 | 1110.5 | 856.3 |
| $^{17}$O NMR (Linewidth @ 50% - MHz) | 45.76 | 45.33 | 46.07 | 106.84 |
| Heavy Metals (Ag, As, Bi, Cd, Cu, Hg, Mo, Pb, Sb, Sn) | <10 ppm | <10 ppm | <10 ppm | <10 ppm |

Example 12

TEER Testing of Acid Water

Figure 9:
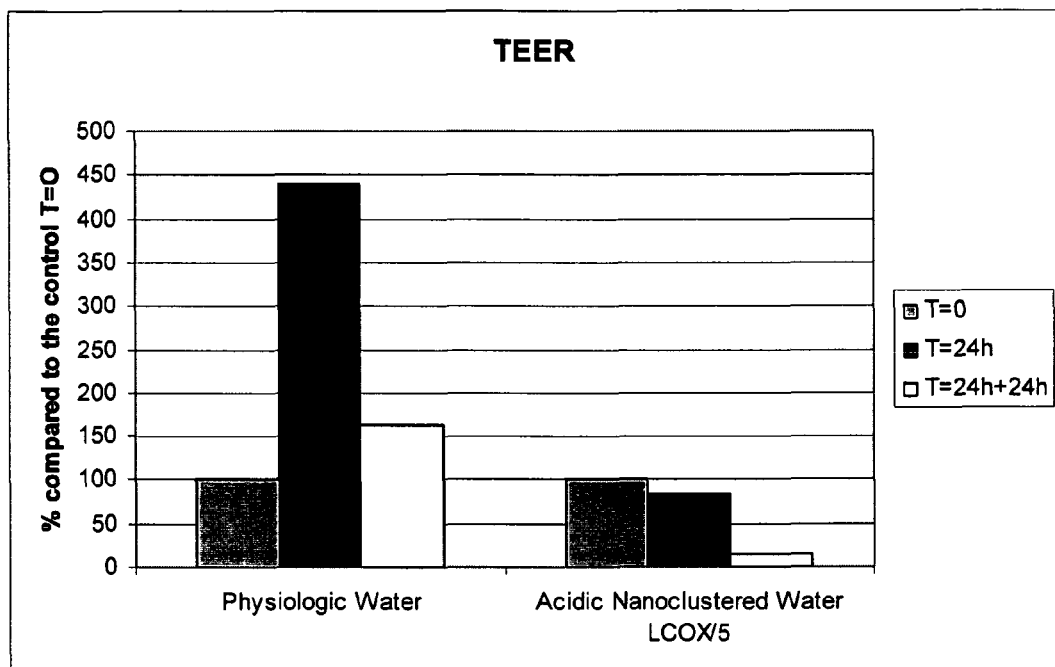
FIGS. 9 and 10 are comparison bar graphs depicting the results of trans-epithelial electrical resistance testing of physiologic water, a tissue sample in acid water meeting the specifications set forth in Table Q, in addition to the formulations described in Table S.
Figure 10:
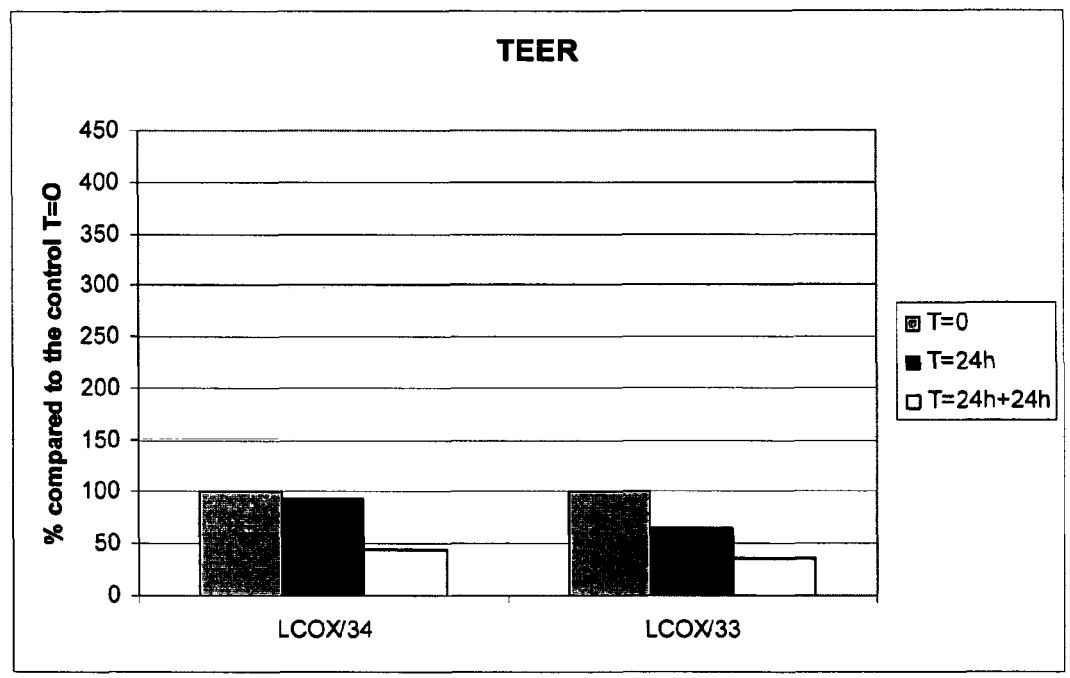

The acid water meeting the specifications set forth in Table Q, in addition to the formulations described in Table S, were tested for their effect on trans-epithelial electrical resistance according to the procedure in Example 7. Results are reported in FIGS. 9-10.

TABLE S

| NAME | BATCH | IDENTIFICATION CODE |
|---|---|---|
| ACIDIC NANOCLUSTERED WATER pH 2.71 | LCOX/5 | LCOX/5 W |
| GEL prepared with DEIONIZED NORMAL WATER ACIDIC by CHLORIDRIC ACID till pH 2.75 | LCOX/34 PLACEBO OF LCOX/33 | LCOX/34 G Pl |
| GEL prepared with ACIDIC NANOCLUSTERED WATER lot LCOX/5 | LCOX/33 | LCOX/33 G |

Example 13

Hydrating Power of Topical Formulations of Acid Water

A dehydrated section of tendon is dipped into the gels described in Tables T and U, and left for 60 minutes and pull out and observed.

TABLE T

| Acid Water of the Present Invention | | | |
|---|---|---|---|
| Raw material Trade Name | INCI Name | Manufacturer | % |
| ACIDIC NANOCLUSTERED WATER | To be assigned | Akuatech | 94.4 |
| Propylene Glycol USP | PROPYLENE GLYCOL | Brenntag | 2.00 |
| Glycerin | GLYCERIN | Sabo | 2.00 |
| Natrosol 250 MR | HYDROXYETHYLCELLULOSE | Hercules | 1.50 |
| Disodium EDTA | Disodium EDTA | Basf | 0.10 |

Appearance: Clear Gel

Color: Colourless

Odour: Characteristic pH at 20° C.: 2.31

Viscosity: 18.500 mPas

TABLE U

| Placebo Gel with Deionised Normal Water Acidified by HCl till pH 2 | | | |
|---|---|---|---|
| Raw material Trade Name | INCI Name | Manufacturer | % |
| DEIONISED NORMAL WATER ACIDIFIED by HCl till pH 2 | AQUA | APR | 94.4 |
| Propylene Glycol USP | PROPYLENE GLYCOL | Brenntag | 2.00 |
| Glycerin | GLYCERIN | Sabo | 2.00 |
| Natrosol 250 MR | HYDROXYETHYLCELLULOSE | Hercules | 1.50 |
| Disodium EDTA | Disodium EDTA | Basf | 0.10 |

Appearance: Clear Gel

Color: Colourless

Odour: Characteristic pH at 20° C.: 2.85

Viscosity: 20.000 mPas

The acidic gel of the present invention resulted in a 40.58% increase in tendon volume. The placebo gel resulted in a 13.43% increase in tendon volume.

Example 14

Efficacy of Acidic Water on In Vitro Wound Healing Process

This example contains a brief description of the method and results obtained to confirm the wound healing process of acidic waters of the present invention, meeting the specifications in Table Q. VitroScreen has developed an experimental in vitro model of skin wound healing on a "Full-thickness skin model (FT)" monitored during 3 days after injury by using positive and negative controls. The biological model has been injured in order to reproduce, in a simplified in vitro model, the molecular response (gene expression) in vivo with a complementary morphological analysis.

mRNA (gene expression) quantification was used to measure various expression parameters that reflect the biochemical and molecular response of the tissue in response to a physical insult. The different phases of the wound healing process are quantified by the following markers:
Epidermis:
Integrine β-1: fundamental for keratinocytes migration
TNF-α: inflammation marker but acting also as a stimulus for the healing process
MMP-9: specific matrix metal protease (gelatinase) directly involved in determining keratinocytes migration
Dermal Compartment
Fibronectin: responsible for the anchoring of cells to the matrix
Collagen I: first collagen type that is destroyed
Collagen VII: newly formed collagen, first sign of tissue regeneration.

The test item, by a micropipette at the dose of 50 μl, has been carefully applied on each tissue injured. One single application has been done on duplicate cultures, daily, for 3 days after the initial injury. Non treated tissues and non treated but injured ones have been used as negative controls.
The following results were obtained:
A significant activity on the expression of Collagen I, Collagen VII and MMP-9: up-regulation observed compared to the control
The same modulation of the control for TNF-α, Fibronectin 1
A non significant modulation of integrin β-1
The activity of the acidic water can thus be summarized as follows:
promoting the modification of the extracellular matrix both at epidermal and dermal level by increasing the expression of Collagen I, VII and MMP-9.
Not differently influencing the inflammatory cascade (TNF-α) from the injured control
Not differently influencing the fibronectin and integrin modulation from the injured control.

Dermacyn® Wound Care is also tested with the same protocol, the results obtained with Dermacyn® Wound Care are similar to the results obtained with the acid water of the present invention.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A composition comprising electrolytic acid water having a pH of 3 or less, a NMR half line width using $^{17}O$ of from about 45 to less than 51 Hz, and an oxide reduction potential (ORP) of from +600 to +1300 mV, wherein said water is further characterized by the following characteristics:
   a) less than 500 mg/l chloride by the mercurimetric method,
   b) from 40 to 70 mg/l of free chlorine measured spectrophotometrically;
   c) from 40 to 70 mg/l of total chlorine measured spectrophotometrically;
   d) from 40 to 70 mg/l of total chlorine measured iodometrically; and
   e) less than 10 mg/l chlorates;
wherein said water maintains characteristics (a), (b), (c), (d), and (e) for greater than 180 days when protected from light, air and heat.

2. The composition of claim 1 wherein said electrolytic acid water is characterized by chemical stability for greater than 180 days when protected from light, air and heat, wherein said chemical stability is defined by no greater than a 10% variation in pH or NMR half line width during said 180 days.

3. The composition of claim 1 in the form of acid water characterized by
   a) less than 10 mg/l of total chlorine measured spectrophotometrically; and
   b) from 100 to 500 mg/l of total chlorine measured iodometrically.

4. The composition of claim 3 in the form of acid water characterized by a NMR half line width using $^{17}O$ of from about 45 to less than 50 Hz, and an oxide reduction potential of from +900 to +1250.

5. The composition of claim 1 in the form an electrolytic acid water having
   a) an oxide reduction potential of greater than 1100, and
   b) less than 10 ppm heavy metals including less than 0.1 ppm yttrium, less than 0.1 ppm zinc, less than 0.1 ppm iridium, less than 0.1 ppm titanium, less than 0.1 ppm zirconium, and less than 0.1 ppm ruthenium.

* * * * *